(12) United States Patent
Henderson et al.

(10) Patent No.: US 11,246,533 B2
(45) Date of Patent: Feb. 15, 2022

(54) INTRAVASCULAR DEVICES, SYSTEMS, AND METHODS HAVING A CORE WIRE WITH MULTIPLE FLATTENED SECTIONS

(71) Applicant: Volcano Corporation, San Diego, CA (US)

(72) Inventors: Eric Henderson, Temecula, CA (US); Mark Richardson, Escondico, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 1005 days.

(21) Appl. No.: 14/805,116

(22) Filed: Jul. 21, 2015

(65) Prior Publication Data
US 2016/0022215 A1    Jan. 28, 2016

Related U.S. Application Data

(60) Provisional application No. 62/027,556, filed on Jul. 22, 2014.

(51) Int. Cl.
| | |
|---|---|
| A61B 5/00 | (2006.01) |
| A61B 5/0215 | (2006.01) |
| A61B 5/026 | (2006.01) |
| A61B 8/12 | (2006.01) |
| A61B 18/14 | (2006.01) |
| A61M 25/09 | (2006.01) |

(52) U.S. Cl.
CPC ............ *A61B 5/6851* (2013.01); *A61B 5/026* (2013.01); *A61B 5/0215* (2013.01); *A61B 8/12* (2013.01); *A61B 18/1492* (2013.01); *A61B 2562/12* (2013.01); *A61M 2025/09075* (2013.01)

(58) Field of Classification Search
CPC ......... A61M 2025/09075; A61M 2025/09058; A61M 2025/09083; A61B 5/0215; A61B 5/6851; A61B 2562/12; A61B 5/026; A61B 5/6852; A61B 5/6855; A61B 5/02152; A61B 5/02158; A61B 5/0265
See application file for complete search history.

(56) References Cited

U.S. PATENT DOCUMENTS

| | | | | |
|---|---|---|---|---|
| 4,953,553 A | * | 9/1990 | Tremulis | A61B 5/0215 600/434 |
| RE35,648 E | * | 11/1997 | Tenerz | A61B 5/0215 600/374 |

(Continued)

*Primary Examiner* — Matthew Kremer
*Assistant Examiner* — Avery M Foley

(57) ABSTRACT

The present disclosure is directed to intravascular devices, systems, and methods having a core wire with multiple flattened sections. In one aspect, a sensing guide wire is provided. The guide wire includes a first flexible elongate member; a sensing element positioned at a distal portion of the first flexible elongate member; and a second flexible elongate member coupled to the first flexible elongate member such that the second flexible elongate member extends distally from the first flexible elongate member; and wherein a distal portion of the first flexible elongate member includes at least two flattened sections, and wherein the first and second flexible elongate members are coupled along a portion of one of the at least two flattened sections. In other aspects, methods of forming a sensing guide wire are provided.

38 Claims, 19 Drawing Sheets

(56) References Cited

U.S. PATENT DOCUMENTS

| | | | | |
|---|---|---|---|---|
| 5,733,248 | A | * | 3/1998 | Adams .............. A61M 25/0041 600/585 |
| 6,203,505 | B1 | * | 3/2001 | Jalisi ................... A61L 29/085 600/585 |
| 7,532,920 | B1 | * | 5/2009 | Ainsworth ......... A61B 5/02007 600/341 |
| 9,955,878 | B2 | | 5/2018 | Burkett |
| 2005/0124917 | A1 | * | 6/2005 | Skujins ................ A61M 25/09 600/585 |
| 2006/0167416 | A1 | * | 7/2006 | Mathis .............. A61B 10/0275 604/164.01 |
| 2007/0027448 | A1 | * | 2/2007 | Paul .................. A61B 18/1492 606/41 |
| 2008/0255629 | A1 | | 10/2008 | Jenson |
| 2011/0015618 | A1 | * | 1/2011 | Satou ............. A61M 25/09016 604/528 |
| 2012/0116383 | A1 | * | 5/2012 | Mauch .............. A61M 25/0147 606/33 |
| 2012/0310081 | A1 | * | 12/2012 | Adler ...................... A61B 8/12 600/427 |
| 2013/0237864 | A1 | * | 9/2013 | Mazar ................ A61B 5/02141 600/488 |
| 2013/0274618 | A1 | * | 10/2013 | Hou .................... A61B 5/6851 600/486 |
| 2013/0317372 | A1 | * | 11/2013 | Eberle ................... G01H 9/004 600/478 |
| 2014/0066791 | A1 | * | 3/2014 | Burkett ............... A61B 5/0215 600/486 |
| 2014/0276109 | A1 | * | 9/2014 | Gregorich ........... A61B 5/0215 600/478 |
| 2017/0128140 | A1 | * | 5/2017 | Samuelsson ............. A61B 5/00 |

* cited by examiner

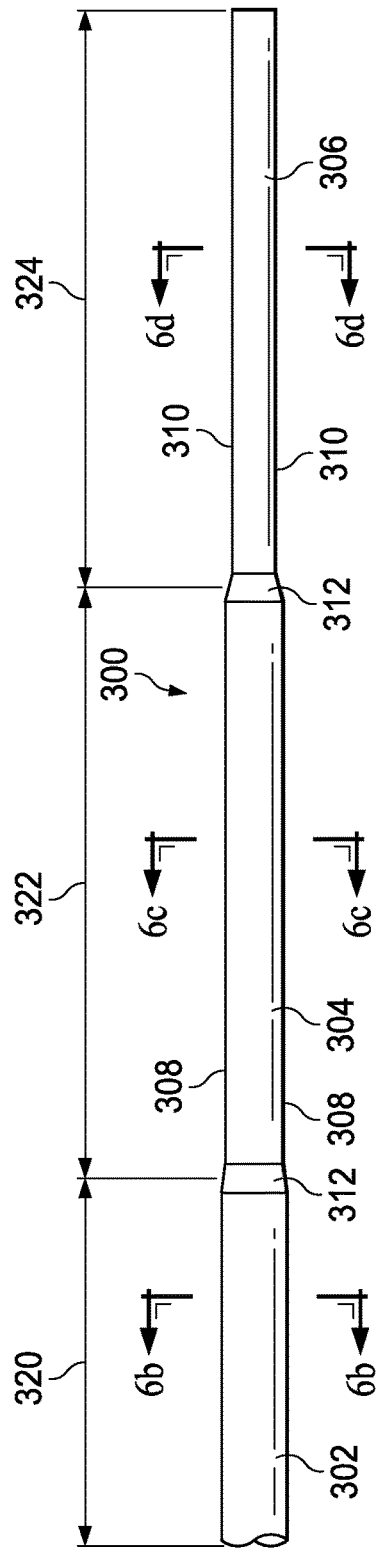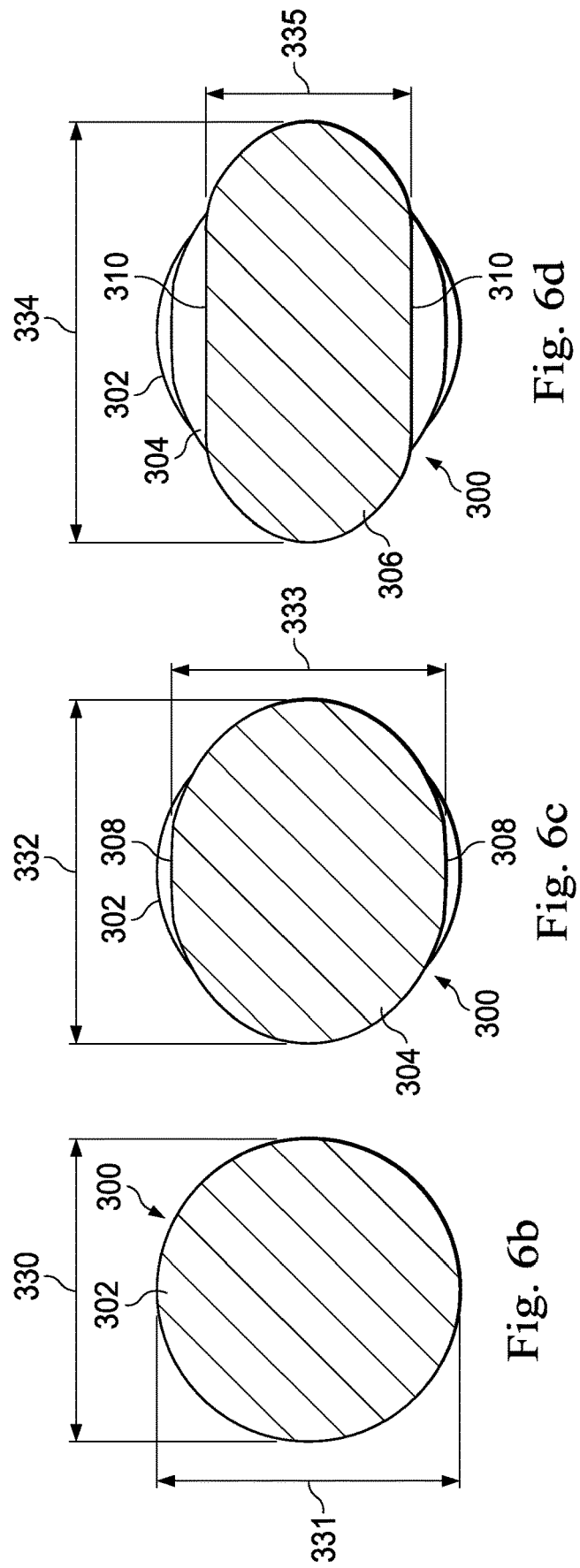

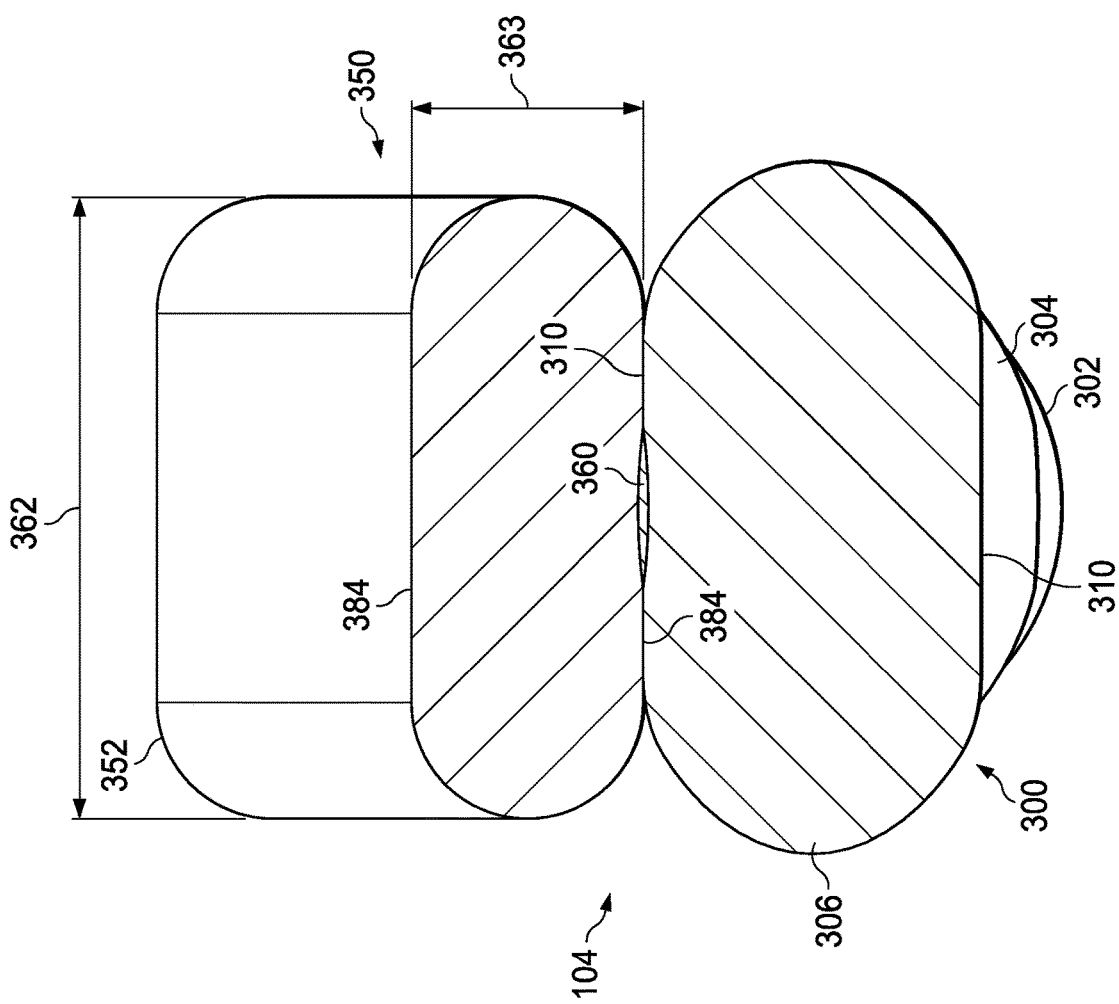

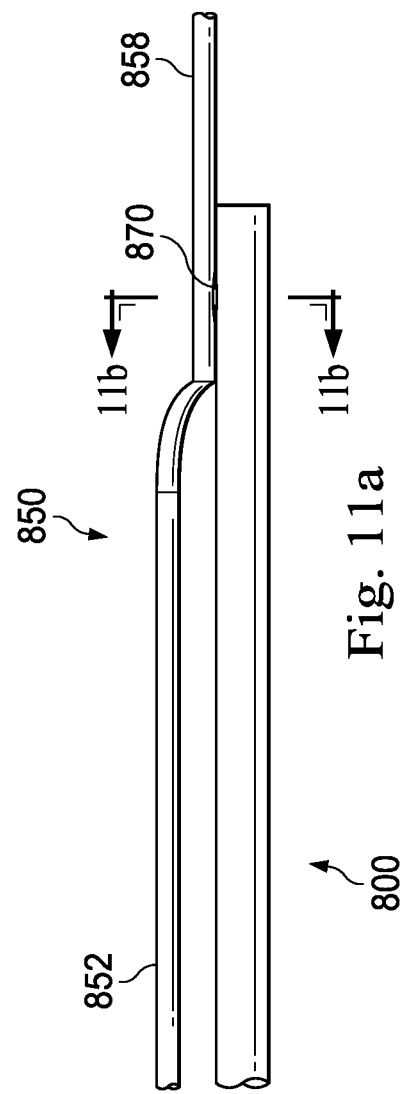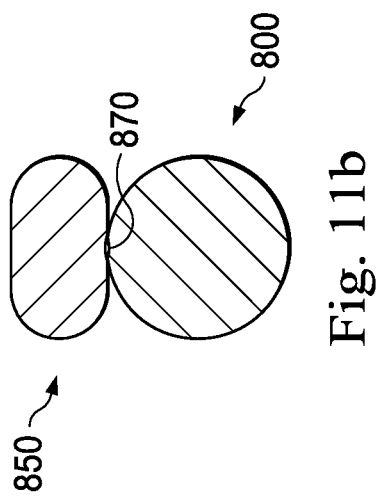
Fig. 11a
Fig. 11b

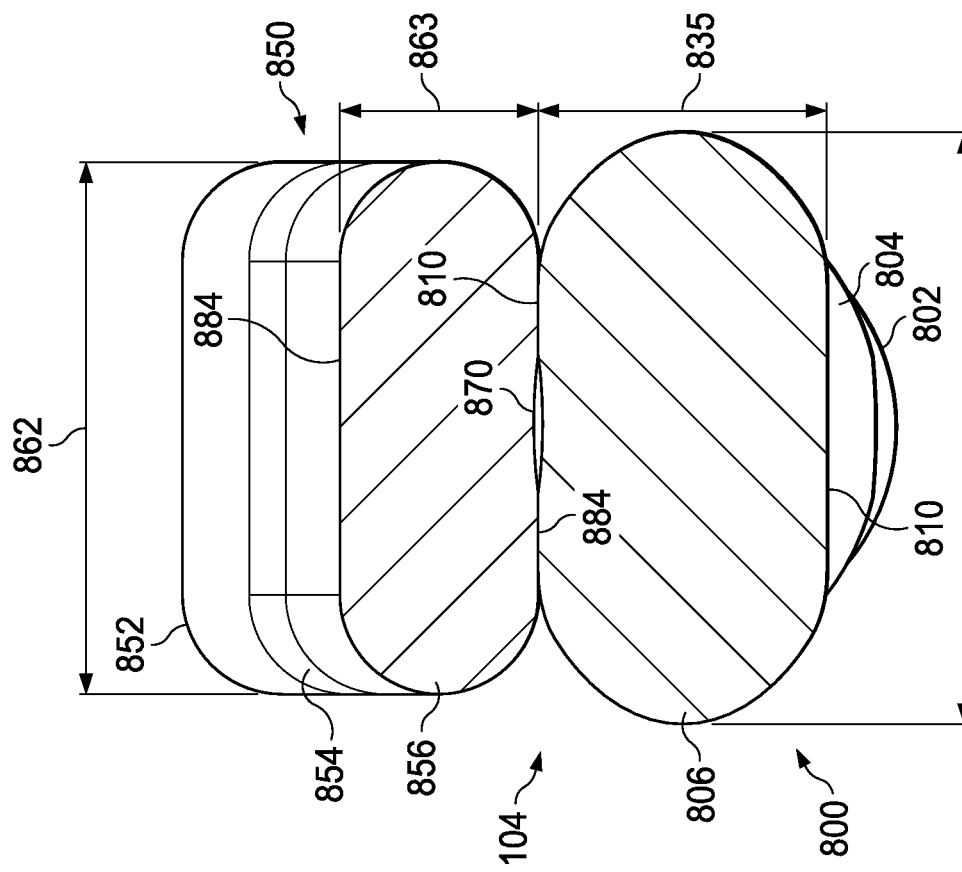
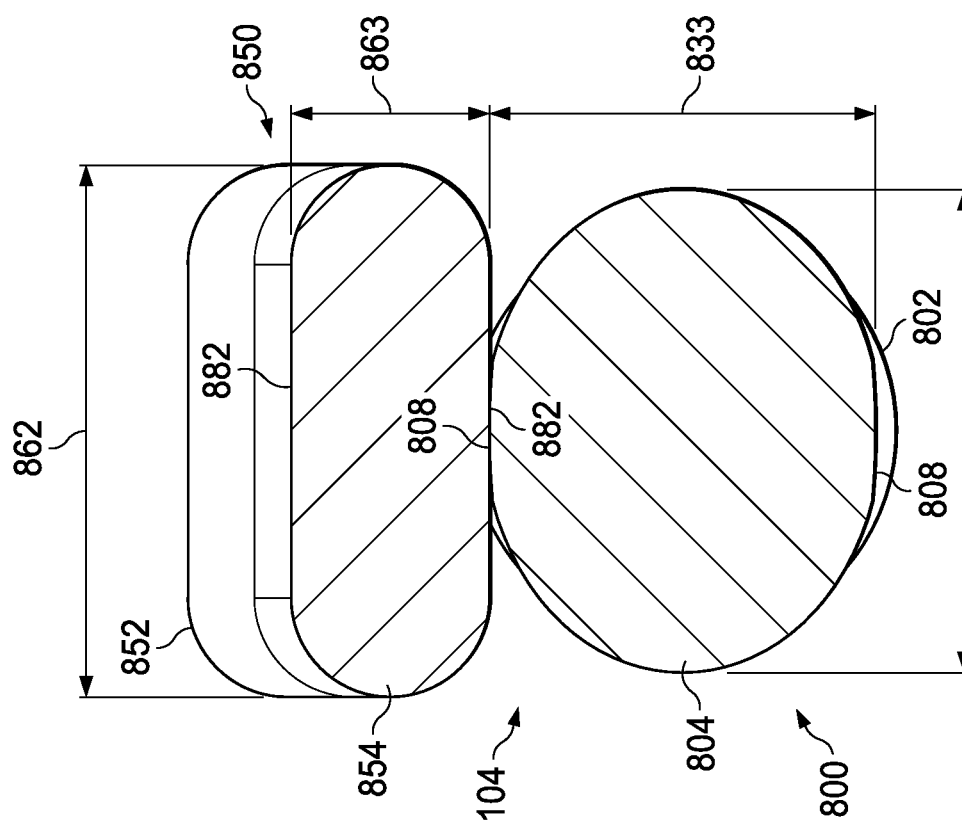

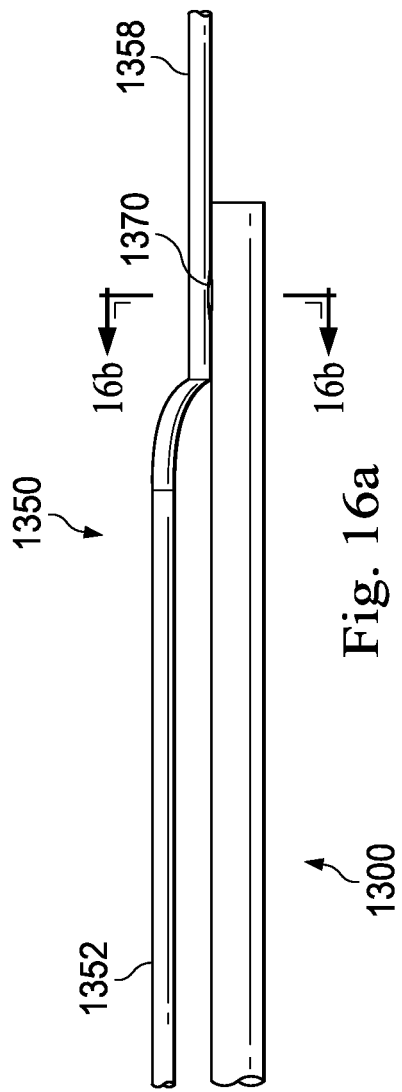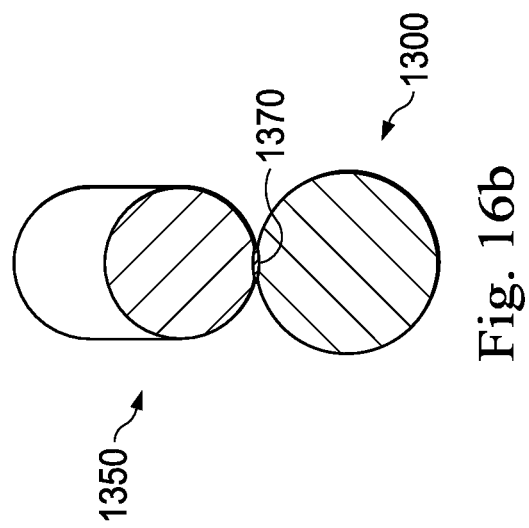

INTRAVASCULAR DEVICES, SYSTEMS, AND METHODS HAVING A CORE WIRE WITH MULTIPLE FLATTENED SECTIONS

CROSS REFERENCE TO RELATED APPLICATIONS

The present application claims priority to and the benefit of the U.S. Provisional Patent Application No. 62/027,556, filed Jul. 22, 2014, which is hereby incorporated by reference in its entirety.

TECHNICAL FIELD

The present disclosure relates to intravascular devices, systems, and methods. In some embodiments, the intravascular devices are guide wires that include a core wire with at least two distal flattened sections to which a shaping ribbon or another core wire is attached.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. Guide wires can include pressure sensors, imaging elements, and/or other electronic, optical, or electro-optical components to obtain such data. A core member generally extends along the length of the guide wire. The one or more components are disposed near the distal portion of the core member. The core member is generally formed of elastic and durable material, which allows the guide wire to traverse the tortuous anatomy, such as a patient's blood vessels. However, the elastic and durable characteristics of the core member also make it difficult for a user to shape the distal tip of the guide wire. It can be important for the distal tip of the guide wire to be shapeable so that the guide wire can be steered through tortuous anatomy.

Conventionally, the distal tip of the guide wire has been formed by attaching a shapeable ribbon to the distal end of the core member. The ribbon is generally tack soldered to the core member. A problem with existing distal tips is that the transition at the tack solder location is not smooth. For example, during use, the tack solder location is a kink point at which the ribbon folds over onto the core member. Such behavior by the distal tip obviates the benefits gained from combining the shapeable ribbon with the durable core member.

Accordingly, there remains a need for improved intravascular devices, systems, and methods that include smooth transition between two components at a distal tip.

SUMMARY

The present disclosure is directed to intravascular devices, systems, and methods that include a guide wire having core wire with two or more flattened portions. A shaping ribbon can be attached to the core wire at the flattened portion(s). The two or more flattened portions provide a smooth transition between the core wire and the shaping ribbon so that the shaping ribbon is less likely to fold over onto the core wire. In some embodiments, second core wire, instead of a shaping ribbon, is attached to the first core wire.

In an exemplary aspect, the present disclosure is directed to a sensing guide wire. The guide wire includes a first flexible elongate member; a sensing element positioned at a distal portion of the first flexible elongate member; and a second flexible elongate member coupled to the first flexible elongate member such that the second flexible elongate member extends distally from the first flexible elongate member; and wherein a distal portion of the first flexible elongate member includes at least two flattened sections, and wherein the first and second flexible elongate members are coupled along a portion of one of the at least two flattened sections.

In an exemplary aspect, the present disclosure is directed to a method of forming a sensing guide wire. The method includes acquiring a first flexible elongate member; shaping a distal portion of the first flexible elongate member to include at least two flattened sections; acquiring a second flexible elongate member; coupling the first and second flexible elongate members along a portion of one of the at least two flattened sections of the first flexible elongate member such that the second flexible elongate member extends distally from the first flexible elongate member; and coupling a sensing element to the first flexible elongate member.

In an exemplary aspect, the present disclosure is directed to a method of forming a sensing guide wire. The method includes: acquiring a first flexible elongate member; acquiring a second flexible elongate member; coupling the first and second flexible elongate members at a distal portion of the first flexible elongate member such that the second flexible elongate member extends distally from the first flexible elongate member; shaping the distal portion of the first flexible elongate member to include at least two flattened sections; coupling a sensing element to the first flexible elongate member.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 5b is a diagrammatic, schematic cross-sectional front view of the core wire of FIG. 5a taken along section line 5b-5b of FIG. 5a.

FIG. 6a is a diagrammatic side view of a core wire of an intravascular device according to aspects of the present disclosure.

FIGS. 6b-6d are diagrammatic, cross-sectional front view of the core wire of FIG. 6a taken along section lines 6b-6b, 6c-6c, and 6d-6d, respectively, of FIG. 6a.

FIG. 7c is a diagrammatic, cross-sectional front view of the distal portion of the intravascular device of FIG. 7b taken along section line 7c-7c of FIG. 7b.

FIG. 10b is a diagrammatic, schematic cross-sectional front view of the core wire of FIG. 10a taken along section line 10b-10b of FIG. 10a.

FIG. 11a is a diagrammatic, schematic side view of a core wire and a shaping ribbon of an intravascular device according to aspects of the present disclosure.

FIG. 11b is a diagrammatic, schematic cross-sectional front view of the core wire and the shaping ribbon of FIG. 11a taken along section line 11b-11b of FIG. 11a.

FIGS. 12b-12c are diagrammatic, cross-sectional front views of the distal portion of the intravascular device of FIG. 12a taken along section lines 12b-12b and 12c-12c, respectively, of FIG. 12a.

FIG. 15b is a diagrammatic, schematic cross-sectional front view of the core wire of FIG. 15a taken along section line 15b-15b of FIG. 15a.

FIG. 16a is a diagrammatic, schematic side view of a core wire and a shaping ribbon of an intravascular device according to aspects of the present disclosure.

FIG. 16b is a diagrammatic, schematic cross-sectional front view of the core wire and the shaping ribbon of FIG. 16a taken along section line 16b-16b of FIG. 16a.

FIGS. 17b-17c are diagrammatic, cross-sectional front views of the distal portion of the intravascular device of FIG. 17a taken along section lines 17b-17b and 17c-17c, respectively, of FIG. 17a.

DETAILED DESCRIPTION

Figure 1:
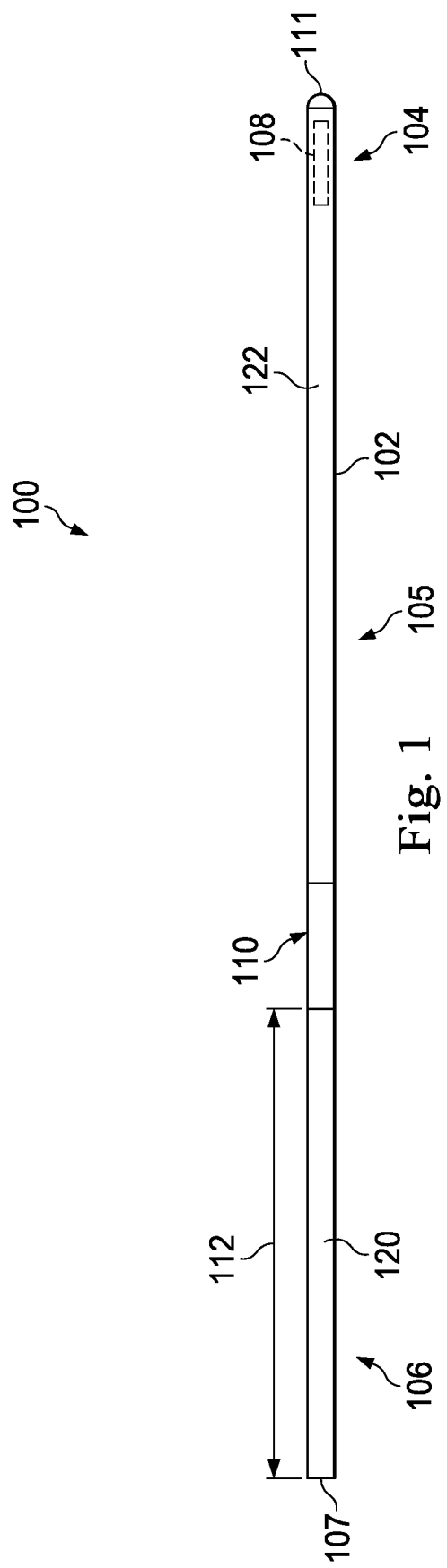
FIG. 1 is a diagrammatic, schematic side view of an intravascular device according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a minor, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Figure 2:
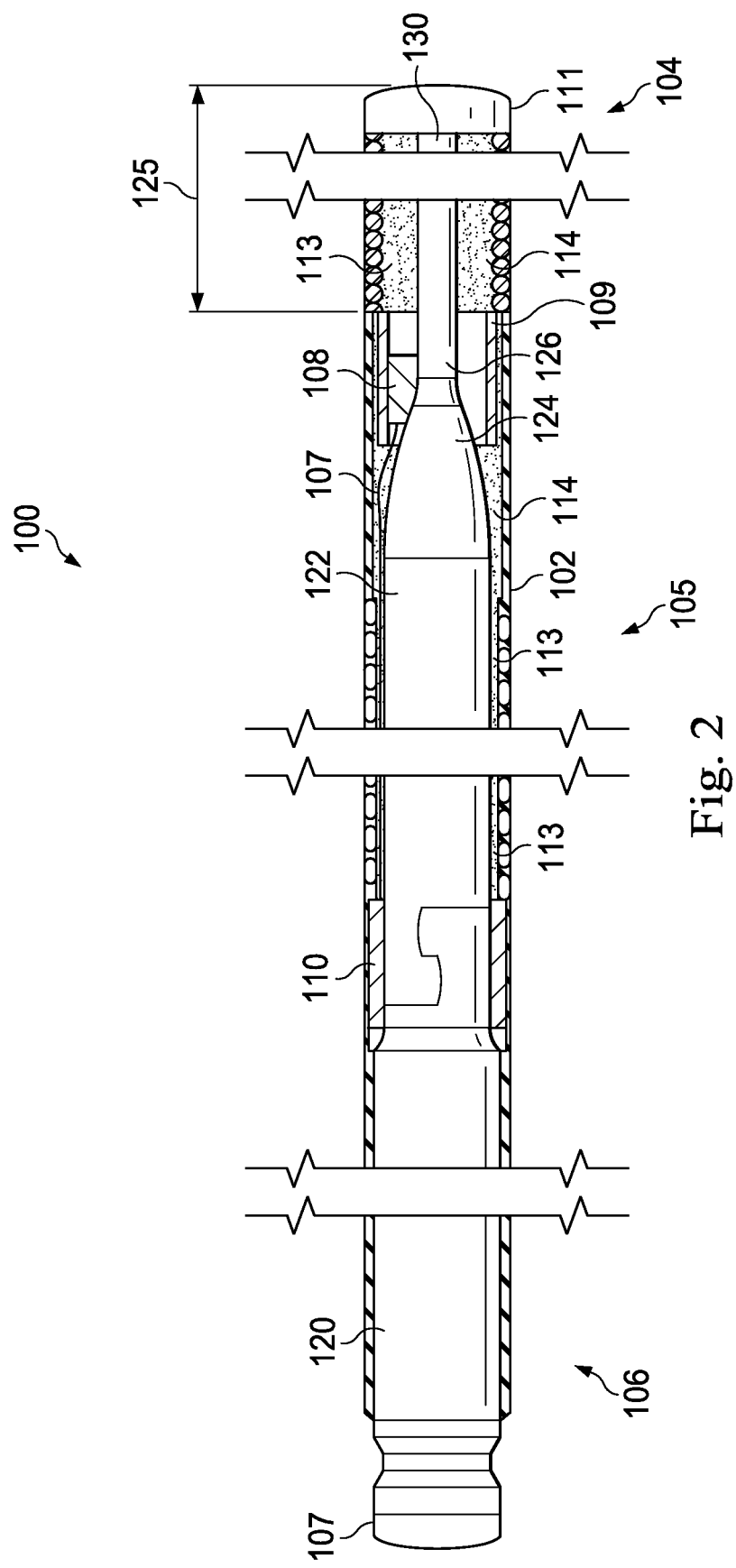
FIG. 2 is a diagrammatic side view of an intravascular device according to aspects of the present disclosure.

FIGS. 1 and 2 illustrate an intravascular device 100 according to aspects of the present disclosure. In that regard, the intravascular device 100 includes a flexible elongate member 102 having a distal portion 104 adjacent a distal tip 111 and a proximal portion 106 adjacent a proximal end 107. The flexible elongate member 102 can include a core member 120 and a core member 122. The core member 120 is disposed at the proximal portion 106 of the flexible elongate member 102, and the core member 122 is disposed along a central portion 105 and the distal portion 104 of the flexible elongate member 102. The core members 120 and 122 can be coupled (e.g., soldered) to one another.

A component 108 is positioned within the distal portion 104 of the flexible elongate member 102 proximal of the distal tip 111. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a minor, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 111. In some instances, the component 108 is positioned within a housing 109. In that regard, the housing 109 is a separate component secured to the core member 122 in some instances. In other instances, the housing 109 is integrally formed as part of the core member 122. For example, a pocket or recess sized and shaped to receive the component 108 can be machine formed at a distal portion of the core member 122.

The intravascular device 100 also includes a connector 110. The connector 110 can be a hypotube positioned such that it surrounds the core members 120 and 122 where the two are coupled (e.g., soldered) to one another. The connector 110 is generally positioned between the core members 120 and 122. The core members 120 and 122 can be any length. As illustrated in FIG. 1, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm.

In some instances, electrical conductors and/or optical pathways associated with the component 108 are embedded within the core of the flexible elongate member 102, as described in U.S. Provisional Patent Application No. 61/935,113, filed Feb. 3, 2014, which is hereby incorporated by reference in its entirety. Generally, any number of electrical conductors, optical pathways, and/or combinations thereof can extend along the length of the flexible elongate member 102, embedded in the core or not. In some instances, between one and ten electrical conductors and/or optical pathways extend along the length of the flexible elongate member 102. The number of communication pathways and the number of electrical conductors and optical pathways extending along the length of the flexible elongate member 102 is determined by the desired functionality of the component 108 and the corresponding elements that define component 108 to provide such functionality.

As illustrated in FIG. 2, The diameter of the core member 122 can be constant along a central portion 105 of the flexible elongate member 102. The central portion 105 of the flexible elongate member 102 can be surrounded by a polyimide sleeve including an embedded coil. The diameter of the core member 122 can decrease adjacent to the distal section 104 of the flexible elongate member 102. In that regard, the core member 122 includes a tapered section 124 with a decreasing diameter. The housing 109 can be coupled to the core member 122 at the tapered section 124. The core member 122 can include a reduced diameter section 126 with diameter that is less than the constant diameter of the core member 122 along the central portion 105 of the flexible elongate member 102. The tapered section 124 and/or the reduced diameter section 126 can be shaped by grinding, ablating, cutting, pressing, etc. As described herein, the reduced diameter section 126 of the core member 122 can include two or more flattened sections. The reduced diameter section 126 can extend at least partially along the distal portion 104 of the flexible elongate member 102.

The central portion 105 and the distal portion 104 of the flexible elongate member 102 can be partially or fully filled with adhesives 113 and 114 that surround the core member 122. The adhesives 113 and 114 can have the same or differing physical characteristics, including flexibility and hardness. For example, adhesive 113 can be medium/low durometer, flexible adhesive, while adhesive 114 can be a low durometer, flexible adhesive. The housing 109 can be surrounded by and/or filled with an adhesive.

The distal portion 104 of the flexible elongate member 102 can include a shaping ribbon 130 coupled to the reduced diameter section 126 of the core member 122. The shaping ribbon 130 can be coupled to various components of the intravascular device 100, including the housing 109 and/or adhesive within and/or surround the housing 109, the core member 122, and/or the distal tip 111. The distal portion 104 of the flexible elongate member 102, including some or all of the reduced diameter section 126 of the core member 122, the shaping ribbon 130, and the distal tip 11, can have length 125. The length 125 can be in the range of about 1 cm to about 25 cm, about 1 cm to about 20 cm, about 1 cm to about 10 cm, etc., including values such 3 cm, 15 cm, 25 cm, etc.

Figure 3:
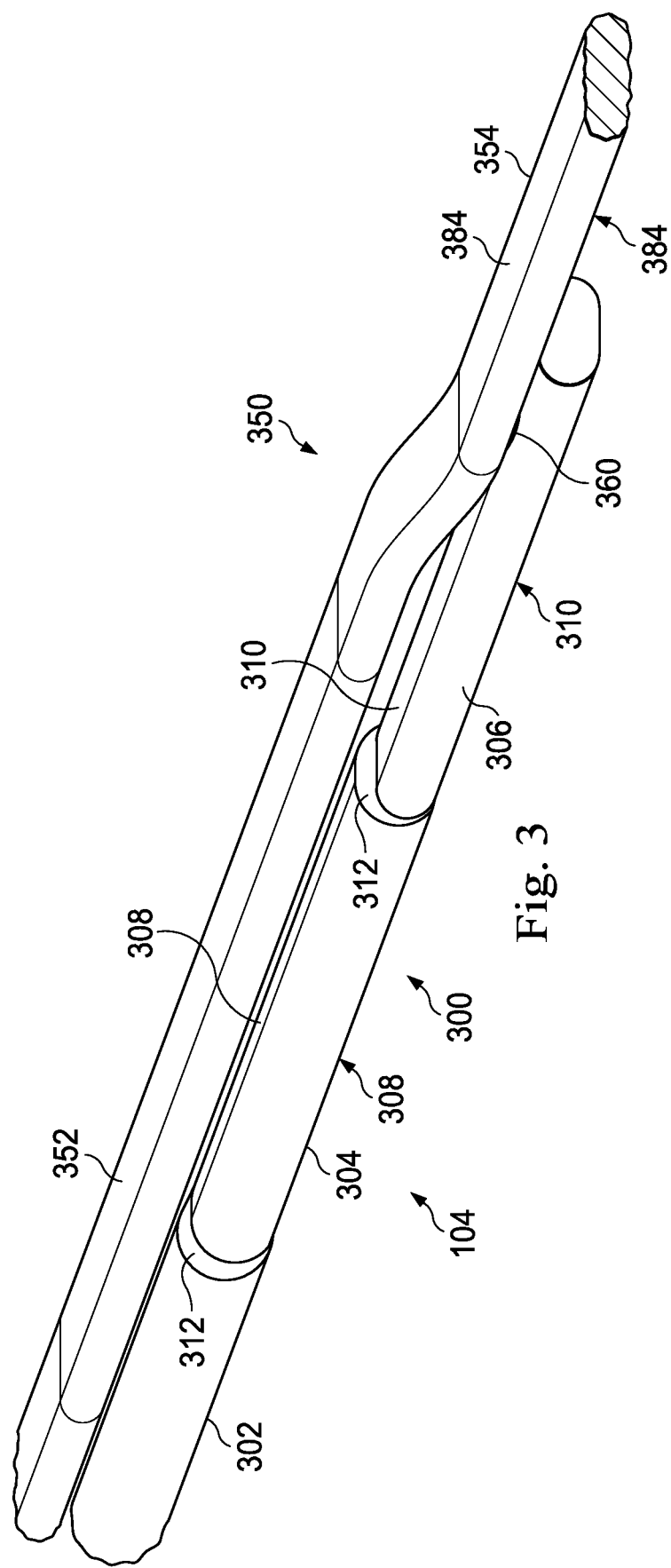
FIG. 3 is a diagrammatic perspective view of a distal portion of an intravascular device according to aspects of the present disclosure.
Figure 4:
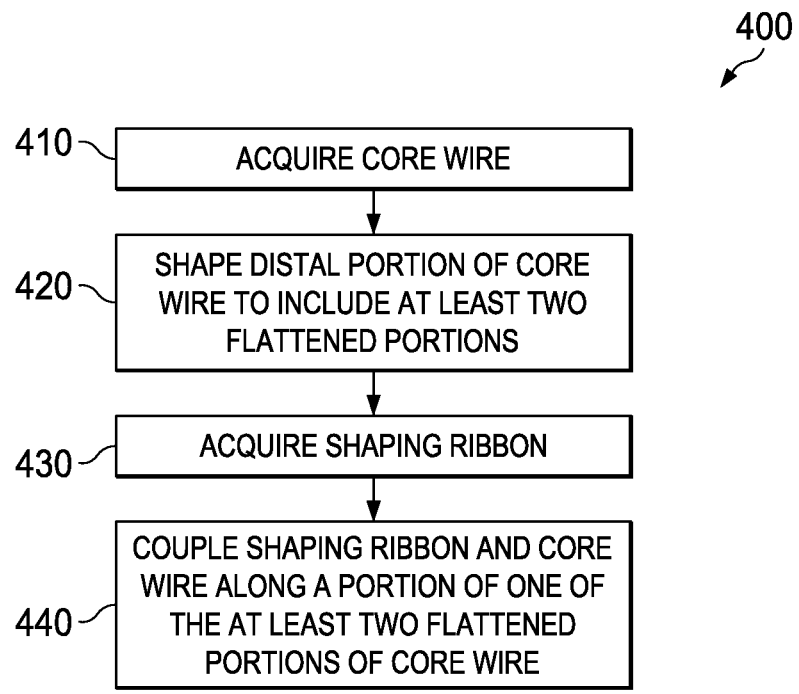
FIG. 4 is a flow diagram of a method of forming an intravascular device according to aspects of the present disclosure.

FIGS. 3-7c illustrate aspects of the distal portion 104 of the intravascular device 100 according to an exemplary embodiment. FIG. 3 illustrates various components of the distal portion 104, including a core wire 300 and a shaping ribbon 350 in an at least partially assembled configuration. FIG. 4 is a flow diagram of a method 400 of forming an intravascular device, such as a sensing guide wire, having the distal portion 104 illustrated in FIG. 3. FIGS. 5a-7c illustrate the distal portion 104 at various stages of the method 400.

As illustrated in FIG. 3, the core wire 300 can include a reduced diameter section 302 and two flattened sections 304, 306. The core wire 300 can be similar to the core member 122 (FIG. 2), and the reduced diameter section 302 can be similar to the reduced diameter section 126 (FIG. 2). The housing 109 (FIG. 2) can be located proximal of the constant diameter section 302. The two flattened sections 304, 306 are adjacent to one another and distal of the constant diameter section 302. In the embodiment of FIG. 3, the flattened section 306 can be described as the distal most flattened section. The core wire 300 can be shaped such that the flattened section 304 includes planar regions 308 on top and bottom surfaces thereof. Similarly, the flattened section 306 includes planar regions 310 on top and bottom surfaces thereof. The core wire 300 can include transition regions 312 disposed between the flattened sections 304, 306 and between the flattened section 304 and the reduced diameter section 302. The transition regions 312 can have a tapered profile as the cross-sectional profile of the core wire 300 changes between the flattened sections 304, 306 and between the flattened section 304 and the reduced diameter section 302.

The shaping ribbon 350 can be coupled to the core wire 300 along at least a portion of one or more of the flattened sections 304, 306. For example, as illustrated in FIG. 3, a solder joint 360 can connect the core wire 300 and the shaping ribbon 350 at a portion of the flattened portion 306 of the core wire 300. In some embodiments, the solder joint 360 can extend along all or some portion of the entire length of one of the flattened sections 304, 306. In some embodiments, the solder joint 360 can extend along all or some portion of both flattened sections 304, 306. The shaping ribbon 350 can include a proximal portion 352 and a distal portion 354. At least a portion of the shaping ribbon 350 coupled to the core wire 300 can include one or more flattened sections. In some embodiments, the entire length of the shaping ribbon 350 is flattened. That is, the shaping ribbon 350 can have a uniform cross-section from its proximal end to its distal end. The shaping ribbon 350 includes planar regions 384 on top and bottom surfaces thereof. The solder joint 360 can be disposed between the bottom planar region 384 of the shaping ribbon 350 and the top planar region 310 of the flattened section 306. The proximal portion 352 can extend proximally from the solder joint 360 and be coupled to the housing 109 (FIG. 2) and/or adhesive within and/or surround the housing 109. The distal portion 354 can extend distally from the solder joint 360 and be coupled to the distal tip 111 (FIGS. 1 and 2).

Figure 5A:
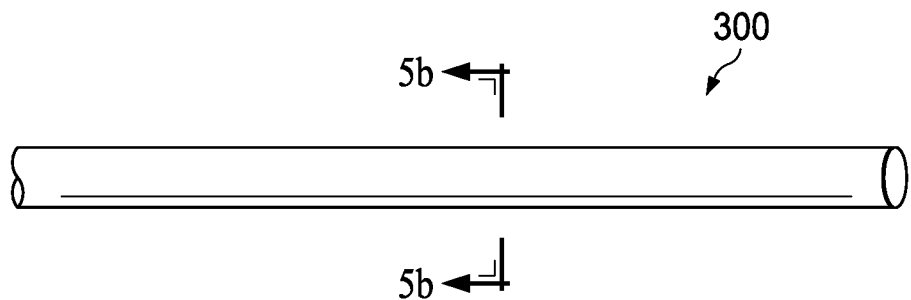
FIG. 5a is a diagrammatic, schematic side view of a core wire of an intravascular device according to aspects of the present disclosure.
Figure 5B:
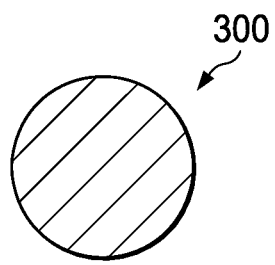

FIG. 4 is a flow diagram of a method 400 of forming the intravascular device 100, including the various components of the distal portion 104 illustrated in FIG. 3. The method 400 can be better understood with reference to FIGS. 5a-7c. It is understood that the core wire 300 and the shaping ribbon 350 are solid components. FIGS. 5b, 6b-6d, and 7c illustrate the cross-sectional contours of the core wire 300 and/or the shaping ribbon 350, and do not illustrate that the core wire 300 and/or the shaping ribbon 350 include a lumen extending therethrough. The method 400 can include, at step 410 acquiring a core member or a core wire. As illustrated in FIGS. 5a-5b, the distal portion of the core wire 300 can have a cylindrical profile with a circular cross-sectional profile. The core wire 300 can be described as a first flexible elongate member. The proximal portion of the core wire 300 illustrated in FIGS. 5a-5b can have a generally constant diameter. As described with respect to FIGS. 1-2, more proximal portions of the core wire 300 can include larger diameters, with constant and/or tapered profiles. The core wire 300 can be formed of a flexible and/or elastic material, including metals or metal alloys such as nickel titanium or nitinol, nickel titanium cobalt, stainless steel, and/or various stainless steel alloys.

Referring again to FIG. 4, the method 400 can include, at step 412, shaping the distal portion of the core wire to include at least two flattened sections. As illustrated in FIGS. 6a-6d, the core wire 300 includes flattened section 304, 306. In some embodiments, shaping the distal portion of the core wire 300 can include cold forming the at least two flattened sections 304, 306, such as by pressing the distal portion with suitable dies. In other embodiments, shaping the distal portion of the core wire 300 can include grinding, ablating, and/or cutting. The lengths 322, 324 of the respective flattened sections 304, 306 can be between about 0.1 cm and about 1.1 cm, about 0.1 cm and 1.0 cm, about 0.1 cm and 0.5 cm, etc., including values such as 0.2 cm, 0.5 cm, 1 cm, etc. In some embodiments, the lengths 322, 324 are the same. For example, in one embodiment, the lengths 322, 324 are 0.5 cm each. In some embodiments, the lengths 322, 324 are different. For example, the length of more proximal flattened sections (e.g., the flattened section 304) can be greater than the length of more distal flattened sections (e.g., the flattened section 306). For example, in one embodiment, length 324 is 0.2 cm and length 322 is 0.5 cm. Thus, in some embodiments, a dimension of the distal most flattened section is different from the dimension of the other flattened sections. In some embodiments, a combined length 342 (FIG. 7a) of the flattened sections 304, 306 is the same regardless of the whether the individual lengths 322, 324 are the same or different. For example, the combined length 342 (FIG. 7a) can be 1 cm.

While only two flattened sections 304, 306 are illustrated, it is understood that the core wire 300 can include one flattened section, or three or more flattened sections in different embodiments. The core wire 300 can be shaped such that the flattened section 304 includes planar regions 308 and the flattened section 306 includes planar regions 310. The planar regions 308, 310 can be disposed on opposite sides of the respective flattened sections 304, 306. For example, in the illustrated embodiment, the planar regions 308, 310 are disposed on top and bottom surfaces of the respective flattened sections 304, 306. In some embodiments, planar regions 308, 310 can be variously positioned around the perimeter of the respective flattened sections 304, 306. In some embodiments, the respective flattened sections 304, 306 include only one planar region 308, 310 (e.g., top planar regions that are adjacent to the shaping ribbon 350). The core wire 300 can also include a reduced diameter section 302. A length 340 of the reduced diameter section 302, between the housing 109 and the proximal most transition region 312 can be, for example, 1 cm.

The cross-sectional profiles of the flattened sections 304, 306 can be different from each other and different from the cross-sectional profile of the reduced diameter section 302. For example, as illustrated in FIG. 6b, the cross-sectional profile of the reduced diameter section 302 is substantially circular. A width 330, a height 331, and/or a diameter of the reduced diameter section 302 can be between about 0.001" and 0.003", about 0.001" and 0.002", etc., including values such as 0.0015", 0.002", 0.00225", etc. As illustrated in FIGS. 6c-6d, the cross-sectional profiles of the respective flattened portions 304, 306 can be substantially non-circular. For example, the cross-sectional profiles of the flattened portions 304, 306 can be substantially oval-shaped. The cross-sectional profile of the flattened portion 304 can be taller than the cross-sectional profile of the flattened portion 306. For example, the height 333 of the flattened portion 304 can be between about 0.001" and 0.003", about 0.001" and 0.002", etc., including values such as 0.0015", 0.00175", 0.002", etc. For example, the height 335 of the flattened portion 306 can be between about 0.001" and 0.003", about 0.001" and 0.002", etc., including values such as 0.00125", 0.0015", 0.00175", etc. The cross-sectional profile of the flattened portion 304 can be wider than the cross-sectional profile of the flattened portion 306. For example, the width 332 of the flattened portion 304 can be between about 0.001" and 0.005", about 0.001" and 0.003", etc., including values such as 0.0015", 0.002", 0.0025", etc. For example, the width 334 of the flattened portion 306 can be between about 0.001" and 0.005", about 0.001" and 0.003", etc., including values such as 0.002", 0.00225", 0.0025", etc. Thus, in some embodiments, a dimension of the distal most flattened section is different from the dimension of the other flattened sections. While the cross-sectional profiles of the reduced diameter section 302 and the flattened sections 304, 306 are shaped differently, the cross-sectional areas can be substantially similar.

Referring again to FIG. 4, the method 400 can include, at step 430, acquiring a shaping ribbon. The shaping ribbon 350 is illustrated, along with the core wire 300, in FIGS. 7a-7c. The shaping ribbon 350 can be described herein as a second flexible elongate member. The shaping ribbon 350 can be formed a shapeable material including, for example, a metal or metal alloy such as stainless steel and/or other suitable materials. Including the shaping ribbon 350 at the distal portion of the intravascular device 100 allows for the tip of the intravascular device to be shaped, allowing the device to be steered efficiently through tortuous anatomy, such as a patient's blood vessels.

In some embodiments, the shaping ribbon 350 can have a cylindrical profile with a circular cross-sectional profile when acquired. In such embodiments, the method 400 can include shaping the shaping ribbon to include one or more flattened sections. For example, an entire length of the shaping ribbon can be flattened. Shaping the shaping ribbon 350 can occur before the shaping ribbon 350 and the core wire 300 are coupled (step 440). In various embodiments, shaping the shaping ribbon 350 can include pressing, grinding, ablating, and/or cutting. For example, shaping the shaping ribbon 350 can be similar to shaping the core wire 300 (step 420). In some embodiments, the shaping ribbon 350 can include the one or more flattened sections when acquired.

The shaping ribbon 350 can include planar regions 384. For example, the planar regions 384 can be disposed on opposite sides of the shaping ribbon 350. For example, in the illustrated embodiment, the planar regions 384 are disposed on top and bottom surfaces of the shaping ribbon 350. In some embodiments, planar regions 384 can be variously positioned around the perimeter of the shaping ribbon 350. In some embodiments, the shaping ribbon 350 includes only one planar region 384 (e.g., a bottom planar region that is adjacent to the core wire 300). The shaping ribbon 350 can have a substantially oval cross-sectional profile. For example, a height 363 of the shaping ribbon 350 can be between about 0.001" and 0.003", about 0.001" and 0.002", etc., including values such as 0.00125", 0.0015", 0.00175", etc. For example, a width 362 of the shaping ribbon 350 can be between about 0.001" and 0.005", about 0.001" and 0.003", etc., including values such as 0.002", 0.00225", 0.0025", etc.

Figure 7A:
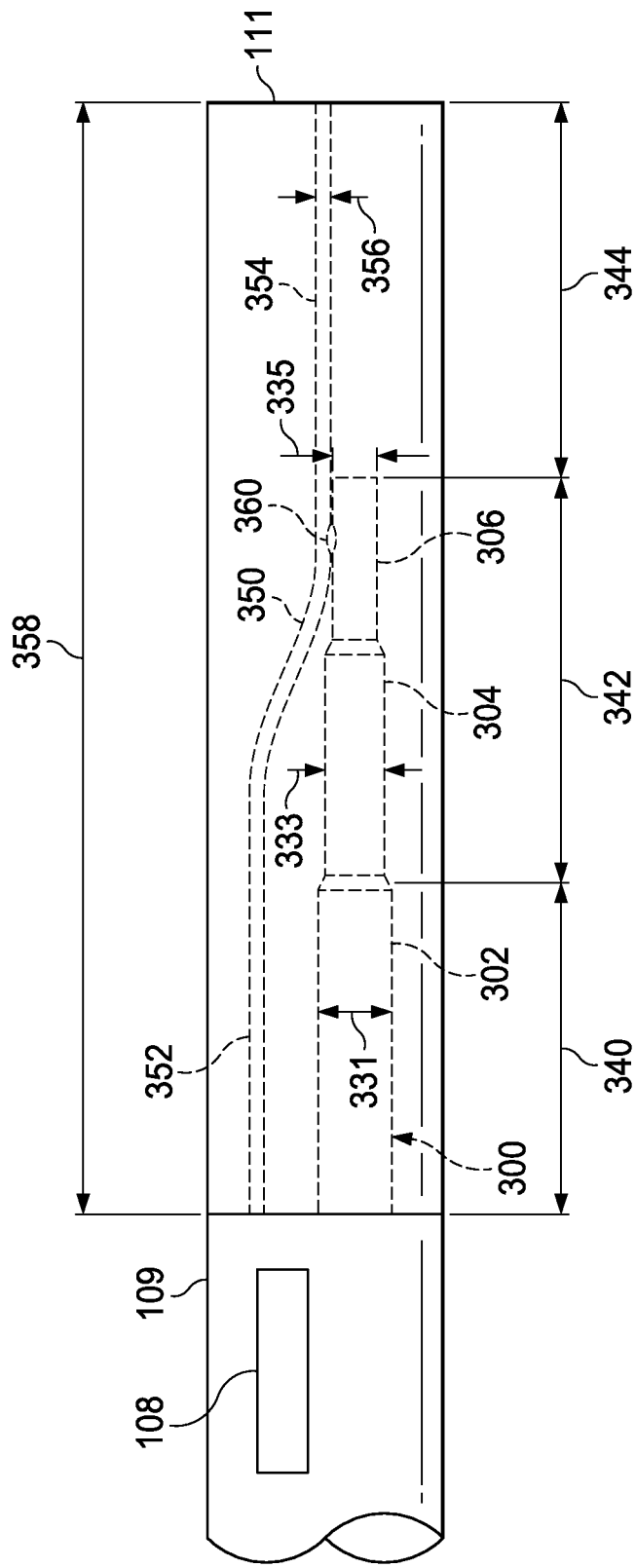
FIG. 7a is a diagrammatic, schematic side view of a distal portion of an intravascular device according to aspects of the present disclosure.
Figure 7B:
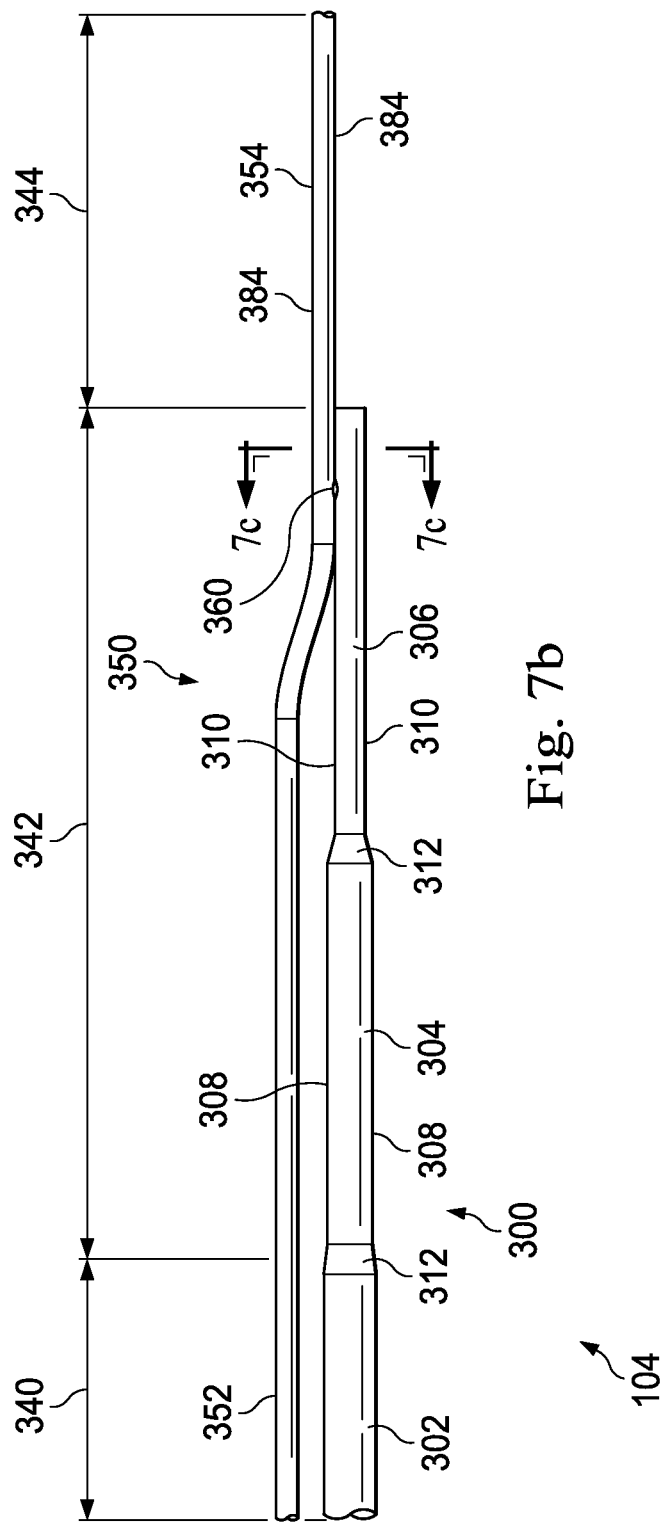
FIG. 7b is a diagrammatic side view of a distal portion of an intravascular device according to aspects of the present disclosure.

Referring again to FIG. 4, the method 400 can include, at step 440, coupling the shaping ribbon and the core wire along a portion of one of the at least two flattened portions of the core wire. As illustrated in FIGS. 7a-7c, a central portion of the shaping ribbon 350 and the core wire 300 can be coupled at the flattened section 306 (e.g., the distal most flattened section). In some embodiments, the solder joint 360 can extend along all or some portion of the entire length of one of the flattened sections 304, 306. In some embodiments, the solder joint 360 can extend along all or some portion of both flattened sections 304, 306. For example, the solder joint 360 can be disposed between the shaping ribbon 350 and the core wire 300. Thus, in some embodiments, coupling the shaping ribbon 350 and the core wire 300 can include introducing solder between the shaping ribbon 350 and the core wire 300, or tack soldering the shaping ribbon 350 and the core wire 300. The solder joint 360 can have a length between about 0.1 cm to about 1 cm, about 0.1 cm to 0.5 cm, etc., including values such as 0.1 cm, 0.25 cm, 0.5 cm, etc. For example, the bottom planar region 384 of the shaping ribbon 350 can be soldered to the top planar region 310 of the core wire 300

In the at least partially assembled configuration shown in FIGS. 7a-7c, the distal portion 354 of the shaping ribbon 350 can extend distally from the core wire 300 and/or the solder joint 360. The distal portion 354 can terminate at and be coupled to the distal tip 111. A proximal portion 352 can extend proximally from the solder joint 360. The proximal portion 352 can terminate at and be coupled to the housing 109 (FIG. 2) and/or adhesive within and/or surround the housing 109. A length 344 of the distal portion 354 of the shaping ribbon 350 (e.g., between the distal end of the core wire 300 and the distal tip 111), the combined length 342 of the flattened portions 304, 306 of the core wire 300, and/or a length 340 of the reduced diameter section 302 of the core wire 300 (e.g., between the housing 109 and the proximal most flattened section) can each be between about 0.1 cm and about 5 cm, about 0.1 cm and 2 cm, about 0.1 cm and 1 cm, etc., including values such as 0.5 cm, 1 cm, 1.5 cm, etc. The lengths 340, 342, 344 can be the same or different in various embodiments. In an exemplary embodiment, the lengths 340, 342, 344 are each 1 cm, such that the length 358 of the distal portion 104 of the intravascular device 100 is 3 cm. The length 358 can be similar to the length 125 (FIG. 2).

In some embodiments, the method 400 can include additional steps to incorporate the element 108 within the intravascular device 100. For example, the method 400 can include coupling the housing 109 to the core wire 300, when the housing 109 is a separate component. The method 400 can include forming a recess within the core member 300. The recess can be sized and shaped to accommodate the element 108. The method 400 can also include coupling the element 108 to the core member 300 (e.g., within the housing 109 or within the recess formed within the core member 300). The element 108 can be positioned at a distal portion of the core member 300. The method 400 can include various other steps to complete assembly of the intravascular device 100, including electrically coupling the element 108 to other component(s) of the intravascular device 100, introducing adhesive(s) into a lumen of the flexible elongate member 102, coupling the core member 120 and the core member 122, introducing a sleeve (e.g., with an integrated coil) around the flexible elongate member 102, introducing a tip coil around the distal portion 104, among others.

Figure 8:
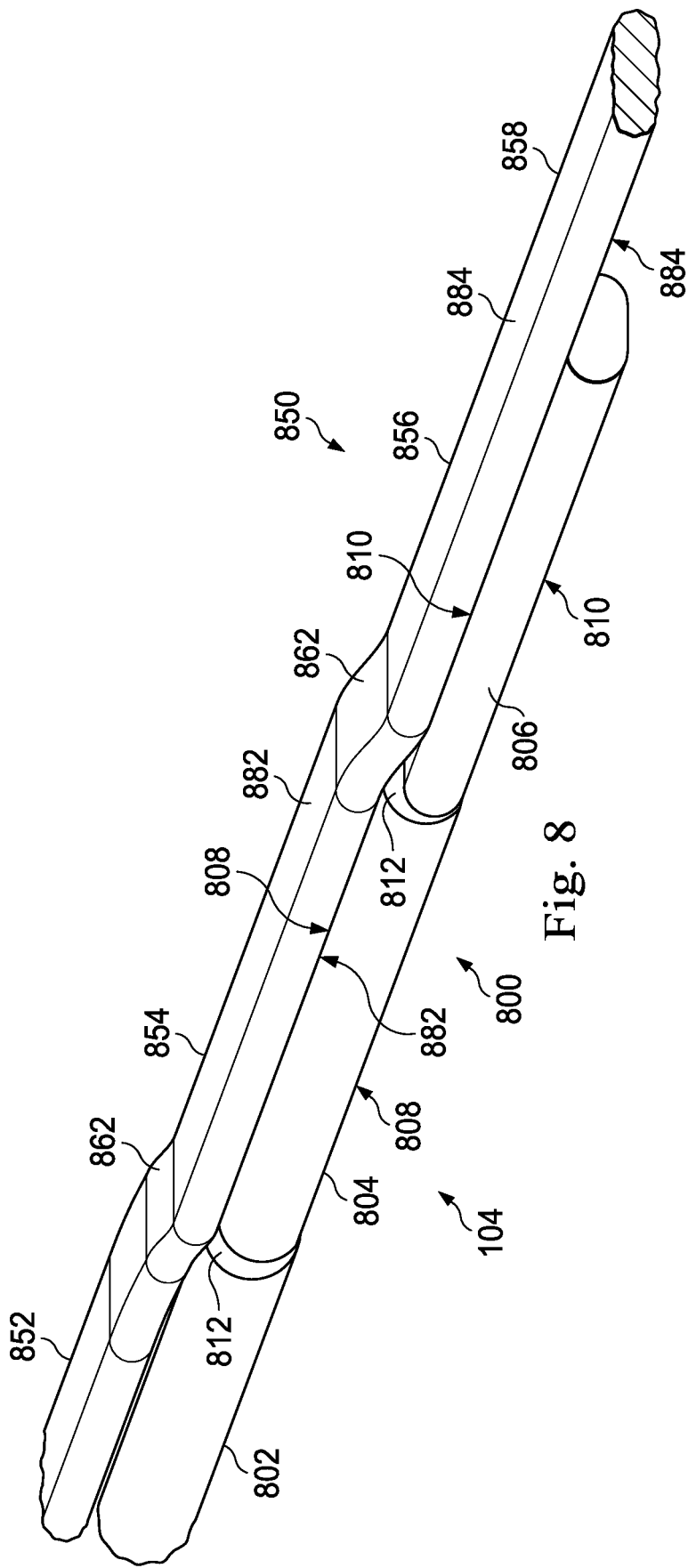
FIG. 8 is a diagrammatic perspective view of a distal portion of an intravascular device according to aspects of the present disclosure.
Figure 9:
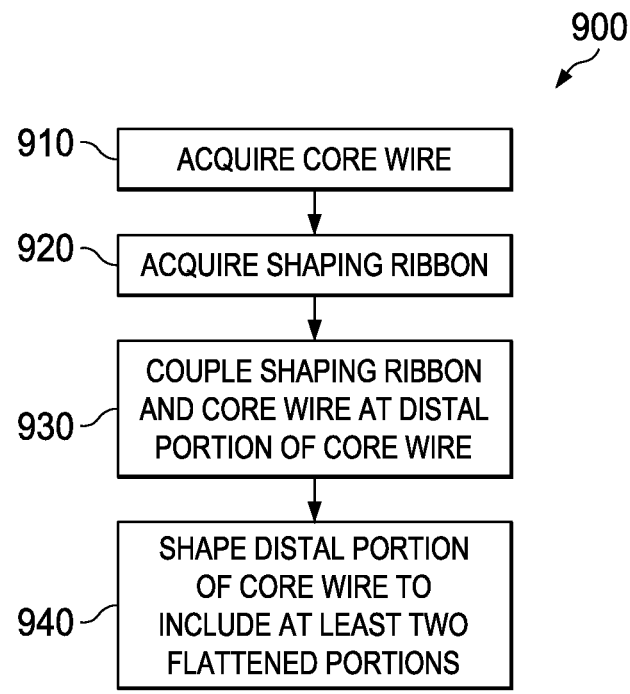
FIG. 9 is a flow diagram of a method of forming an intravascular device according to aspects of the present disclosure.

FIGS. 8-12c illustrate aspects of the distal portion 104 of the intravascular device 100 according to an exemplary embodiment. FIG. 8 illustrates various components of the distal portion 104, including a core member 800 and a shaping ribbon 850 in an at least partially assembled configuration. FIG. 9 is a flow diagram of a method 900 of forming an intravascular device, such as a sensing guide wire, having the distal portion 104 illustrated in FIG. 8. FIGS. 10a-12c illustrate the distal portion 104 at various stages of the method 900.

As illustrated in FIG. 8, the core member 800 can include a reduced diameter section 802 and two flattened sections 804, 806. The core member 800 can be similar to the core member 122 (FIG. 2) and the core member 300 (FIG. 3). The reduced diameter section 802 can be similar to the reduced diameter section 126 (FIG. 2) and the reduced diameter section 302 (FIG. 3). The housing 109 (FIG. 2) can be located proximal of the constant diameter section 802. The two flattened sections 804, 806 are adjacent to one another and distal of the constant diameter section 802. In the embodiment of FIG. 8, the flattened section 806 can be described as the distal most flattened section of the core member 800. The core member 800 can be shaped such that the flattened section 804 includes planar regions 808 on top and bottom surfaces thereof. Similarly, the flattened section 806 includes planar regions 810 on top and bottom surfaces thereof. The core member 800 can include transition regions 812 disposed between the flattened sections 804, 806 and between the flattened section 804 and the reduced diameter section 802. The transition regions 812 can have a tapered profile as the cross-sectional profile of the core wire 800 changes between the flattened sections 804, 806 and between the flattened section 804 and the reduced diameter section 802.

The shaping ribbon 850 can be coupled to the core member 800 along a portion of one or more of the flattened sections 804, 806. In some embodiments, a solder joint can extend along all or some portion of the entire length of one of the flattened sections 806, 808. In some embodiments, the solder joint can extend along all or some portion of both flattened sections 806, 808. For example, the shaping ribbon 850 and the core member 800 can be coupled at the flattened section 806. The flattened section 806 can include a solder joint to connect the shaping ribbon 850 and the core member 800. For example, the shaping ribbon 850 and the core member 800 can be coupled at two or more of the flattened sections 804, 806. Solder can be disposed along both flattened sections 804, 806 to connect the shaping ribbon 850 and the core member 800.

The shaping ribbon 850 can include two or more flattened sections 854, 856. In some embodiments, the entire length of the shaping ribbon 850 is flattened. That is, the shaping ribbon 850 can have a uniform cross-section from its proximal end to its distal end. The two flattened sections 854, 856 are adjacent to one another and positioned between the proximal portion 852 and the distal portion 858. The flattened sections 854, 856 of the shaping ribbon 850 can be longitudinally aligned with the flattened portions 804, 806 of the core member 800. The shaping ribbon 850 can be shaped such that the flattened section 854 includes planar regions 882 on top and bottom surfaces thereof. Similarly, the flattened section 856 includes planar regions 884 on top and bottom surfaces thereof. A solder joint can be disposed between the bottom planar region 884 of the shaping ribbon 850 and the top planar region 810 of the flattened section 806 and/or between the bottom planar region 882 of the shaping ribbon 850 and the top planar region 808 of the flattened section 804. The shaping ribbon 850 can include transition regions 862 disposed between the flattened sections 854, 856 and between the flattened section 854 and the proximal portion 852. The transition regions 862 of the shaping ribbon 850 can be aligned with the transition regions 812 of the core member 800. The proximal portion 852 of the shaping ribbon 850 can extend proximally from the flattened sections 854, 856, and be coupled to the housing 109 (FIG. 2) and/or adhesive within and/or surround the housing 109. The distal portion 854 can extend distally from the flattened sections 854, 856, and be coupled to the distal tip 111 (FIGS. 1 and 2).

Figure 10A:
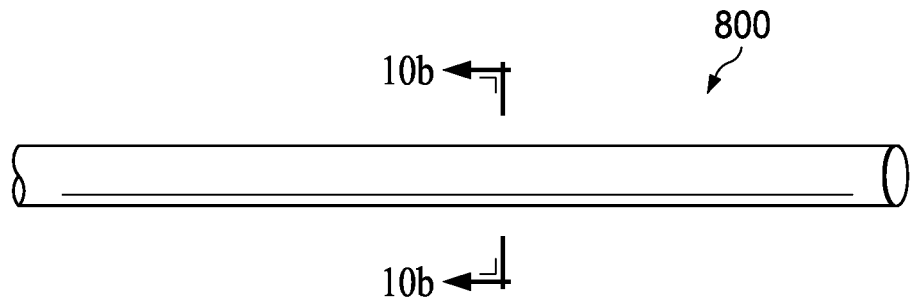
FIG. 10a is a diagrammatic, schematic side view of a core wire of an intravascular device according to aspects of the present disclosure.
Figure 10B:
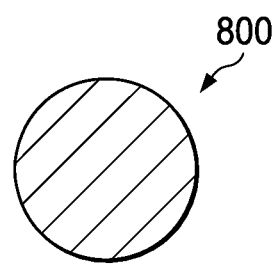

FIG. 9 is a flow diagram of a method 900 of forming the intravascular device 100, including the various components of the distal portion 104 illustrated in FIG. 8. The method 900 can be better understood with reference to FIGS. 10a-12c. It is understood that the core wire 800 and the shaping ribbon 850 are solid components. FIGS. 10b, 11b, 12b, and 12c illustrate the cross-sectional contours of the core wire 800 and/or the shaping ribbon 850, and do not illustrate that the core wire 800 and/or the shaping ribbon 850 include a lumen extending through. The method 900 can include, at step 910 acquiring a core member or a core wire. The distal portion of the core wire 800 is illustrated in FIGS. 10a-10b. The core wire 800 can be similar to the core wire 122 and/or core wire 300 (FIG. 3), and can be similarly described as a first flexible elongate member.

Referring again to FIG. 9, the method 900 can include, acquiring a shaping ribbon. The shaping ribbon 850 is illustrated, along with the core wire 800, in FIGS. 11a-11b. The shaping ribbon 850 can be similar to the shaping ribbon 350 (FIG. 3) and can be similarly described as a second flexible elongate member. The cross-sectional profile of the shaping ribbon 850 is shown to include one or more flattened sections in FIGS. 11a-11b. In some embodiments, the shaping ribbon 850 can include the one or more flattened sections when acquired. In some embodiments, the shaping ribbon 850 can have a cylindrical profile with a circular cross-sectional profile when acquired. In such embodiments, the method 900 can include shaping the shaping ribbon to include one or more flattened sections. For example, an entire length of the shaping ribbon can be flattened. In some embodiments, shaping the shaping ribbon 850 can occur before the shaping ribbon 850 and the core wire 800 are coupled (step 930). In various embodiments, shaping the shaping ribbon 850 can include pressing, grinding, ablating, and/or cutting. For example, shaping the shaping ribbon 850 can be similar to shaping the core wire 800 (step 940), as described below.

Referring again to FIG. 9, the method 900 can include, at step 930, coupling the shaping ribbon and the core wire at a distal portion of the core wire. As illustrated in FIGS. 11a-11b, a central portion of the shaping ribbon 850 and the core wire 800 can be coupled at a distal portion of the core wire. For example, a solder joint 870 can be disposed between the shaping ribbon 850 and the distal portion of the core wire 800. Thus, in some embodiments, coupling the shaping ribbon 850 and the core wire 800 can include introducing solder between the shaping ribbon 850 and the core wire 800. The solder joint 870 can have a length between about 0.1 cm to about 2 cm, about 0.1 cm to about 1 cm, about 0.1 cm to 0.5 cm, etc., including values such as 0.25 cm, 0.5 cm, 0.75 cm, etc. In some embodiments, solder can be introduced multiple times during the method 900 to couple the shaping ribbon 850 and the core wire 800. For example, solder can be introduced between the shaping ribbon 850 and the core wire 800 during step 930 and again when the distal portion of the core wire 800 is shaped to include at least two flattened portions (step 940).

Figure 12A:
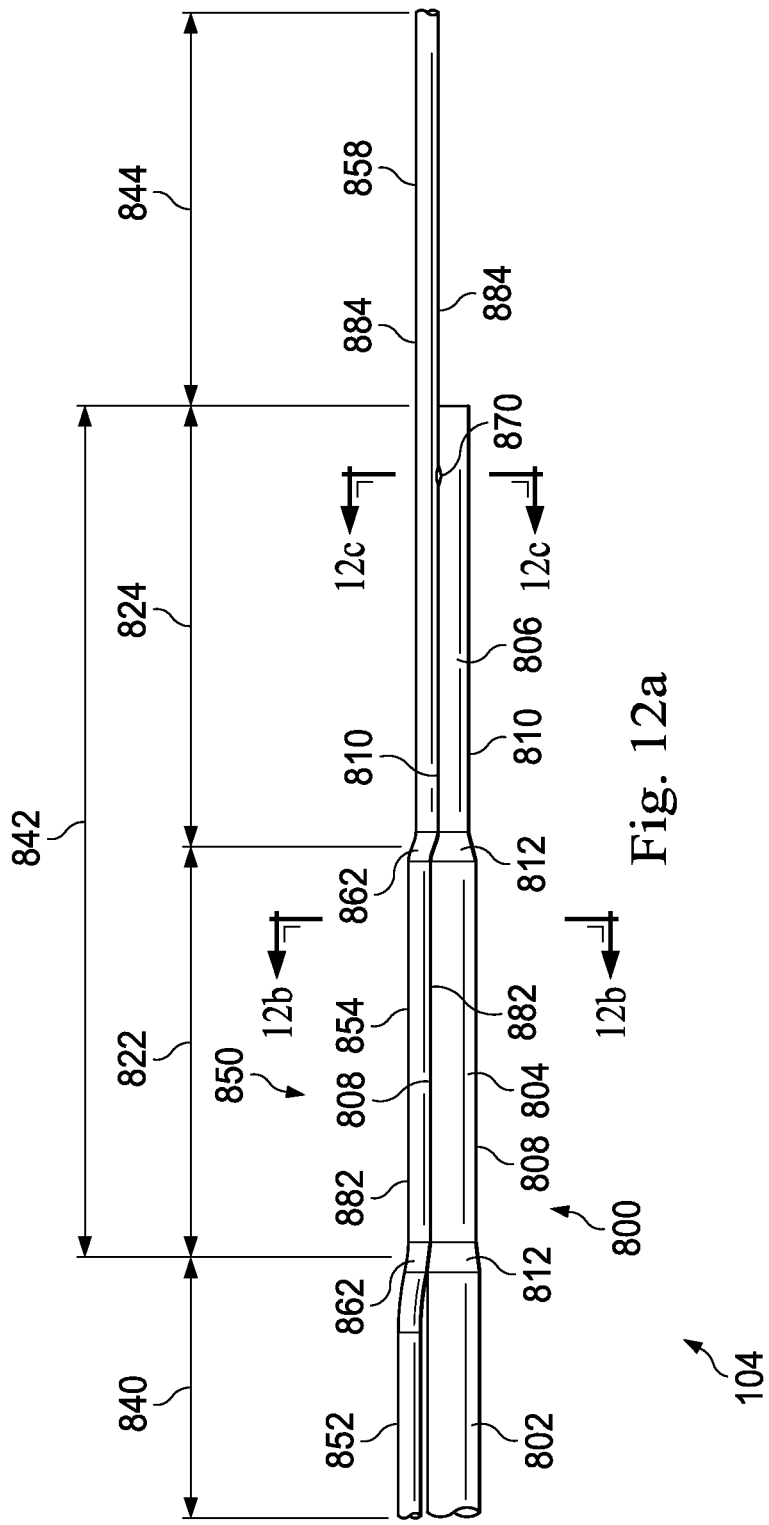
FIG. 12a is a diagrammatic side view of a distal portion of an intravascular device according to aspects of the present disclosure.

Referring again to FIG. 9, the method 900 can include, at step 940, shaping the distal portion of the core wire to include at least two flattened sections. As illustrated in FIGS. 12a-12c, the core wire 800 includes flattened sections 804, 806. Shaping the distal portion of the core wire 800 can include cold forming the at least two flattened sections 804, 806, such as by pressing core wire 800 with suitable dies. The distal portion of the core wire 800 can be shaped such that the respective flattened sections of the core wire 800 and the shaping ribbon 850 are longitudinally aligned. Pressure can be applied to the distal portion of the core wire 800 to form the flattened sections 804, 806 while the shaping ribbon 850 is coupled to the core wire 800. Thus, the pressure that shapes the core wire 800 can be also experienced by the shaping ribbon 850. That is, the applied pressure can shape both the core wire 800 and the shaping ribbon 850.

In some embodiments, the method 900 can include introducing solder between the shaping ribbon 850 and the core wire 800 as pressure is being applied to the shaping ribbon and/or the core wire. For example, solder can be introduced at a distal most flattened section (e.g., flattened section 806) of the core wire 800. For example, solder can be introduced along two or more of the flattened sections (e.g., flattened sections 804, 806) of the core wire 800. Introducing additional solder when the shaping ribbon 850 and/or the core wire 800 is shaped can ensure that the coupling between the shaping ribbon and the core wire remains after pressure is applied. For example, the bottom planar region 884 of the flattened section 856 of the shaping ribbon 850 can be soldered to the top planar region 810 of the core wire 800 and/or the bottom planar region 882 of the shaping ribbon 850 can be soldered to the top planar region 808 of the core wire 800.

The flattened sections 804, 806 of the core wire 800 can be similar to the respective flattened sections 304, 306 (FIG. 6a-6d) of the core wire 300. For example, the lengths 822, 824 of the respective flattened sections 804, 806 can be between about 0.1 cm and about 1 cm, about 0.1 cm and 0.8 cm, about 0.1 cm and 0.6 cm, etc., including values such as 0.5 cm, 0.6 cm, 0.8 cm, etc. In some embodiments, a combined length 842 of the flattened sections 804, 806 is the same regardless of the whether the individual lengths 822, 824 are the same or different. For example, the combined length 842 can be 1 cm. A reduced diameter section 802 can be similar to the reduced diameter section 302 (FIGS. 6a-6b). For example, a length 840 of the reduced diameter section 802, between the housing 109 and the proximal most transition region 812 can be, for example, 1 cm.

While only two flattened sections 804, 806 of the core wire 800 are illustrated, it is understood that the core wire 800 can include one flattened section, or three or more flattened sections in different embodiments. The core wire 800 can be shaped such that the flattened section 804 includes planar regions 808 and the flattened section 806 includes planar regions 810. The planar regions 808, 810 can be similar to the planar regions 308, 310 (FIGS. 6a-6d).

The cross-sectional profiles of the flattened sections 804, 806 can be different from each other and different from the cross-sectional profile of the reduced diameter section 802. The cross-sectional profiles of the flattened sections 804, 806 and the reduced diameter section 802 can be similar to the respective cross-sectional profiles of the flattened section 304, 306 and the reduced diameter section 302. In that regard, the cross-sectional profile of the flattened portion 804 can be taller than the cross-sectional profile of the flattened portion 806. For example, the height 833 of the flattened portion 804 can be between about 0.001" and 0.003", about 0.001" and 0.002", etc., including values such as 0.0015", 0.00175", 0.002", etc. For example, the height 835 of the flattened portion 806 can be between about 0.001" and 0.003", about 0.001" and 0.002", etc., including values such as 0.00125", 0.0015", 0.00175", etc. The cross-sectional profile of the flattened portion 804 can be wider than the cross-sectional profile of the flattened portion 806. For example, the width 832 of the flattened portion 804 can be between about 0.001" and 0.005", about 0.001" and 0.003", etc., including values such as 0.0015", 0.002", 0.0025", etc. For example, the width 834 of the flattened portion 806 can be between about 0.001" and 0.005", about 0.001" and 0.003", etc., including values such as 0.002", 0.00225", 0.0025", etc.

The flattened sections 854, 856 of the shaping ribbon 850 can include planar regions 882, 884, respectively. The planar regions 882, 884 can be similar to the planar regions 384 (FIG. 7b-7c). Generally, in the illustrated embodiment of FIGS. 12a-12c, the cross-sectional profiles of the flattened sections 854, 856 are substantially oval shaped. The cross-sectional profiles can also be described as rectangular with rounded sides. The dimensions of the cross-sectional profiles of the flattened sections 882, 884 can be the same or similar. For example, a height 863 of the flattened sections 882, 884 of the shaping ribbon 850 can be between about 0.001" and 0.003", about 0.001" and 0.002", etc., including values such as 0.00125", 0.0015", 0.00175", etc. For example, a width 862 of the flattened sections 882, 884 of the shaping ribbon 850 can be between about 0.001" and 0.005", about 0.001" and 0.003", etc., including values such as 0.002", 0.00225", 0.0025", etc. While only two flattened sections 854, 856 of the shaping ribbon 850 are illustrated, it is understood that the shaping ribbon can include one flattened section, or three or more flattened sections in different embodiments.

In the at least partially assembled configuration shown in FIGS. 12a-12c, the distal portion 858 of the shaping ribbon 850 can extend distally from the core wire 800 and/or the solder joint 870. The distal portion 858 can terminate at and be coupled to the distal tip 111. A proximal portion 852 can extend proximally from the solder joint 870 and/or the proximal most flattened section (e.g., flattened section 854) of the shaping ribbon 850. The proximal portion 852 can terminate at and be coupled to the housing 109 (FIG. 2) and/or adhesive within and/or surround the housing 109. A length 844 of the distal portion 854 of the shaping ribbon 850 (e.g., between the distal end of the core wire 800 and the distal tip 111), the combined length 842 of the flattened portions 804, 806 of the core wire 800, and/or a length 840 of the reduced diameter section 802 of the core wire 800 (e.g., between the housing 109 and the proximal most flattened section) can each be between about 0.1 cm and about 5 cm, about 0.1 cm and 2 cm, about 0.1 cm and 1 cm, etc., including values such as 0.5 cm, 1 cm, 1.5 cm, etc. The lengths 840, 842, 844 can be similar to the lengths 340, 342, 344 (FIGS. 7a-7b).

In some embodiments, the method 900 can include additional steps to incorporate the element 108 within the intravascular device 100. For example, the method 900 can include coupling the housing 109 to the core wire 800, when the housing 109 is a separate component. The method 900 can include forming a recess within the core member 800. The recess can be sized and shaped to accommodate the element 108. The method 400 can also include coupling the element 108 to the core member 800 (e.g., within the housing 109 or within the recess formed within the core member 800). The element 108 can be positioned at a distal portion of the core member 800. The method 900 can include various other steps to complete assembly of the intravascular device 100, including electrically coupling the element 108 to other component(s) of the intravascular device 100, introducing adhesive(s) into a lumen of the flexible elongate member 102, coupling the core member 120 and the core member 122, introducing a sleeve (e.g., with an integrated coil) around the flexible elongate member 102, introducing a tip coil around the distal portion 104, among others.

Figure 13:
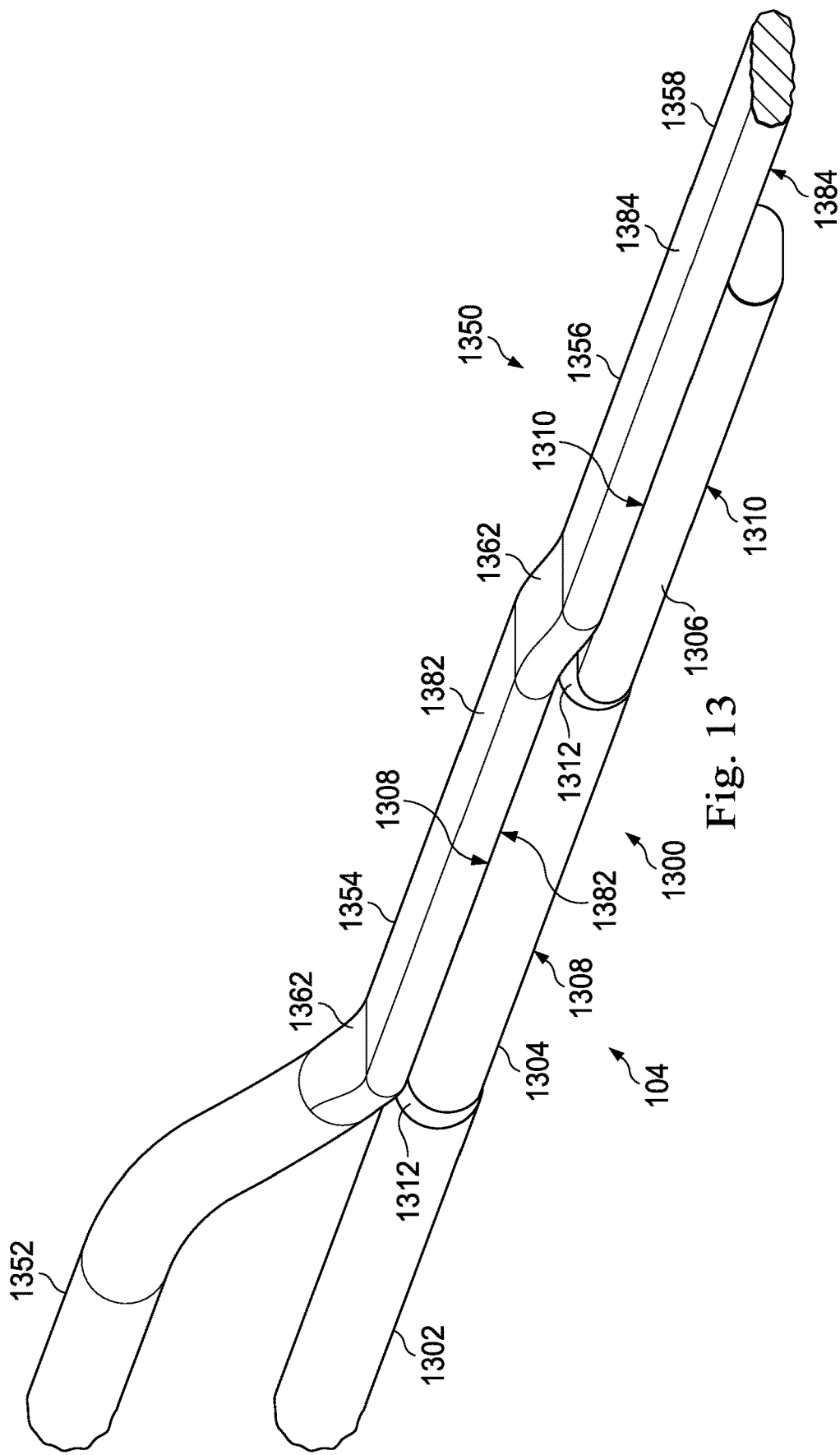
FIG. 13 is a diagrammatic perspective view of a distal portion of an intravascular device according to aspects of the present disclosure.
Figure 14:
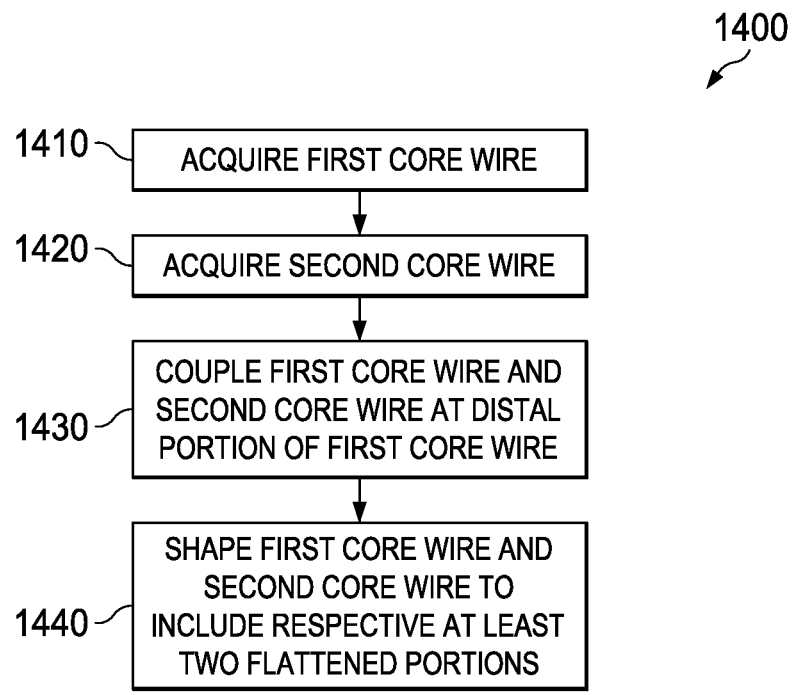
FIG. 14 is a flow diagram of a method of forming an intravascular device according to aspects of the present disclosure.
Figure 15A:
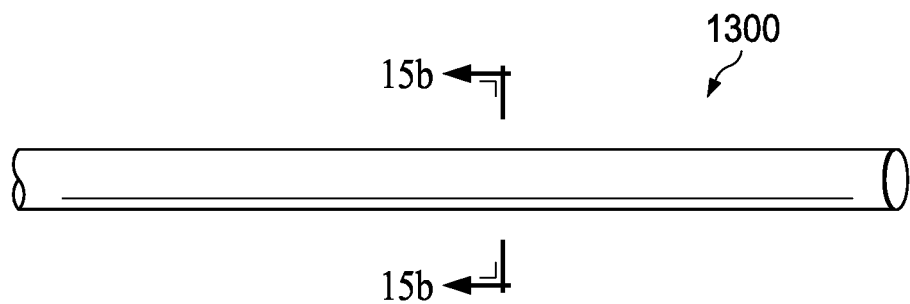
FIG. 15a is a diagrammatic, schematic side view of a core wire of an intravascular device according to aspects of the present disclosure.
Figure 15B:
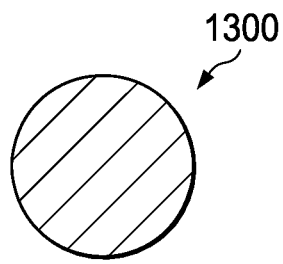

FIGS. 13-17c illustrate aspects of the distal portion 104 of the intravascular device 100 according to an exemplary embodiment. FIG. 13 illustrates various components of the distal portion 104, including a core wire 1300 and a core wire 1350 in an at least partially assembled configuration. FIG. 14 is a flow diagram of a method 1400 of forming an intravascular device, such as a sensing guide wire, having the distal portion 104 illustrated in FIG. 13. FIGS. 15a-17c illustrate the distal portion 104 at various stages of the method 1400.

The embodiment of the distal portion 104 of the intravascular device 100 illustrated and described with respect FIGS. 13-17c is substantially similar to the embodiment illustrated and described with respect to FIGS. 8-12c. The embodiment of FIGS. 13-17c includes two core wires: the core wire 1300 having at least two flattened portions, and a core wire 1350 coupled to and extending distally from the core wire 1300. The core wire 1350 can have a smaller diameter compared to the core wire 1300. Recall that the embodiment of FIGS. 8-12c included the core wire 800 having at least two flattened sections, and the shaping ribbon 850 coupled to and extending distally from the core wire 800. In the embodiments of FIGS. 13-17c, the core wire 1350 assumes the role of the shaping ribbon 850. Using two core wires can allow for more efficient manufacturing of the intravascular device 100 because no particular orientation for the core wire 1350 need be maintained when coupling the core wires 1300, 1350 and/or when forming the respective at least two flattened sections of the core wires 1300, 1350.

As illustrated in FIG. 13, the core wire 1300 can include a reduced diameter section 1302 and two flattened sections 1304, 1306. The core wire 1300 can be similar to the core wire 122 (FIG. 2), the core wire 300 (FIG. 3), and/or the core wire 800 (FIG. 8). The reduced diameter section 1302 can be similar to the reduced diameter section 126 (FIG. 2), the reduced diameter section 302 (FIG. 3), and/or the reduced diameter section 802 (FIG. 8). The housing 109 (FIG. 2) can be located proximal of the constant diameter section 1302. The two flattened sections 1304, 1306 are adjacent to one another and distal of the constant diameter section 1302. In the embodiment of FIG. 13, the flattened section 1306 can be described as the distal most flattened section of the core wire 1300. The core wire 1300 can be shaped such that the flattened section 1304 includes planar regions 1308 on top and bottom surfaces thereof. Similarly, the flattened section 1306 includes planar regions 1310 on top and bottom surfaces thereof. The core wire 1300 can include transition regions 1312 disposed between the flattened sections 1304, 1306 and between the flattened section 1304 and the reduced diameter section 1302. The transition regions 1312 can have a tapered profile as the cross-sectional profile of the core wire 1300 changes between the flattened sections 1304, 1306 and between the flattened section 1304 and the reduced diameter section 1302.

The core wire 1350 can be coupled to the core wire 1300 along a portion of one or more of the flattened sections 1304, 1306. In some embodiments, a solder joint can extend along all or some portion of the entire length of one of the flattened sections 1306, 1308. In some embodiments, the solder joint can extend along all or some portion of both flattened sections 1306, 1308. For example, the core wire 1350 and the core wire 1300 can be coupled at the flattened section 1306. The flattened section 1306 can include a solder joint to connect the core wire 1350 and the core wire 1300. For example, the core wire 1350 and the core wire 1300 can be coupled at two or more of the flattened sections 1304, 1306. Solder can be disposed both flattened sections 1304, 1306 to connect the core wire 1350 and the core wire 1300.

The core wire 1350 can include two or more flattened sections 1354, 1356. In some embodiments, the entire length of the shaping ribbon 1350 is flattened. That is, the shaping ribbon 1350 can have a uniform cross-section from its proximal end to its distal end. The two flattened sections 1354, 1356 are adjacent to one another and positioned between the proximal portion 1352 and the distal portion 1358. The flattened sections 1354, 1356 of the core wire 1350 can be longitudinally aligned with the flattened portions 1304, 1306 of the core member 1300. The core wire 1350 can be shaped such that the flattened section 1354 includes planar regions 1382 on top and bottom surfaces thereof. Similarly, the flattened section 1356 includes planar regions 1384 on top and bottom surfaces thereof. A solder joint can be disposed between the bottom planar region 1384 of the core wire 1350 and the top planar region 1310 of the flattened section 1306 and/or between the bottom planar region 1382 of the core wire 1350 and the top planar region 1308 of the flattened section 1304. The core wire 1350 can include transition regions 1362 disposed between the flattened sections 1354, 1356 and between the flattened section 1354 and the proximal portion 1352. The transition regions 1362 of the core wire 1350 can be aligned with the transition regions 1312 of the core wire 1300. The proximal portion 1352 of the core wire 1350 can extend proximally from the flattened sections 1354, 1356, and be coupled to the housing 109 (FIG. 2) and/or adhesive within and/or surround the housing 109. The distal portion 1354 can extend distally from the flattened sections 1354, 1356, and be coupled to the distal tip 111 (FIGS. 1 and 2).

FIG. 14 is a flow diagram of a method 1400 of forming the intravascular device 100, including the various components of the distal portion 104 illustrated in FIG. 13. The method 1400 can be better understood with reference to FIGS. 15*a*-17*c*. It is understood that the core wire 1300 and the shaping ribbon 1350 are solid components. FIGS. 15*b*, 16*b*, 17*b*, and 17*c* illustrate the cross-sectional contours of the core wire 1300 and/or the shaping ribbon 1350, and do not illustrate that the core wire 1300 and/or the shaping ribbon 1350 include a lumen extending therethrough. The method 1400 can include, at step 1410 acquiring a first core member or a first core wire. The distal portion of the core wire 1300 is illustrated in FIGS. 10*a*-10*b*. The core wire 1300 can be similar to the core wire 300 (FIG. 3) and/or the core wire 800 (FIG. 8), and can be similarly described as a first flexible elongate member.

Referring again to FIG. 14, the method 1400 can include, acquiring a second core wire. The core wire 1350 is illustrated, along with the core wire 1300, in FIGS. 16*a*-16*b*. The core 1350 can be described herein as a second flexible elongate member. The diameter of the core wire 1300 and/or the core wire 1350 is in the range of about 0.001" to about 0.004", about 0.001" to about 0.003", about 0.001" to about 0.002", etc., including values such as 0.0015", 0.002", 0.0025", etc. In some embodiments, the core wire 1350 can have a smaller diameter compared to the core wire 1300. The core wire 1300 and/or the core wire 1350 can be formed a shapeable material including, for example, a metal or metal alloy such as stainless steel and/or other suitable materials. Including the core wire 1350 at the distal portion of the intravascular device 100 allows for the intravascular device to be steered efficiently through the tortuous anatomy, such as a patient's blood vessels.

As illustrated in FIGS. 16*a*-16*b*, the core wire 1350 can have a cylindrical profile with a circular cross-sectional profile when acquired. In such embodiments, the method 1400 can include shaping the second core wire to include two or more flattened sections. As described below, shaping the core wire 1350 can occur after the core wire 1350 and the core wire 1300 are coupled (step 1430) and simultaneously as the distal portion of the core wire 1300 is shaped to include at least two flattened portions (step 1440).

Referring again to FIG. 14, the method 1400 can include, at step 1430, coupling the first core wire and the second core wire at a distal portion of the first core wire. As illustrated in FIGS. 16*a*-16*b*, a central portion of the core wire 1350 and the core wire 1300 can be coupled at a distal portion of the core wire 1300. For example, a solder joint 1370 can be disposed between the core wire 1350 and the distal portion of the core wire 1300. Thus, in some embodiments, coupling the core wire 1350 and the core wire 1300 can include introducing solder between the core wire 1350 and the core wire 1300. The solder joint 1370 can have a length between about 0.1 cm to about 2 cm, about 0.1 cm to about 1 cm, about 0.1 cm to 0.5 cm, etc., including values such as 0.25 cm, 0.5 cm, 0.75 cm, etc. In some embodiments, solder can be introduced multiple times during the method 1400 to couple the core wire 1350 and the core wire 1300. For example, solder can be introduced between the core wire 1350 and the core wire 1300 during step 1430 and again when the core wires 1300, 1350 are shaped to include respective at least two flattened portions (step 1340).

Figure 17A:
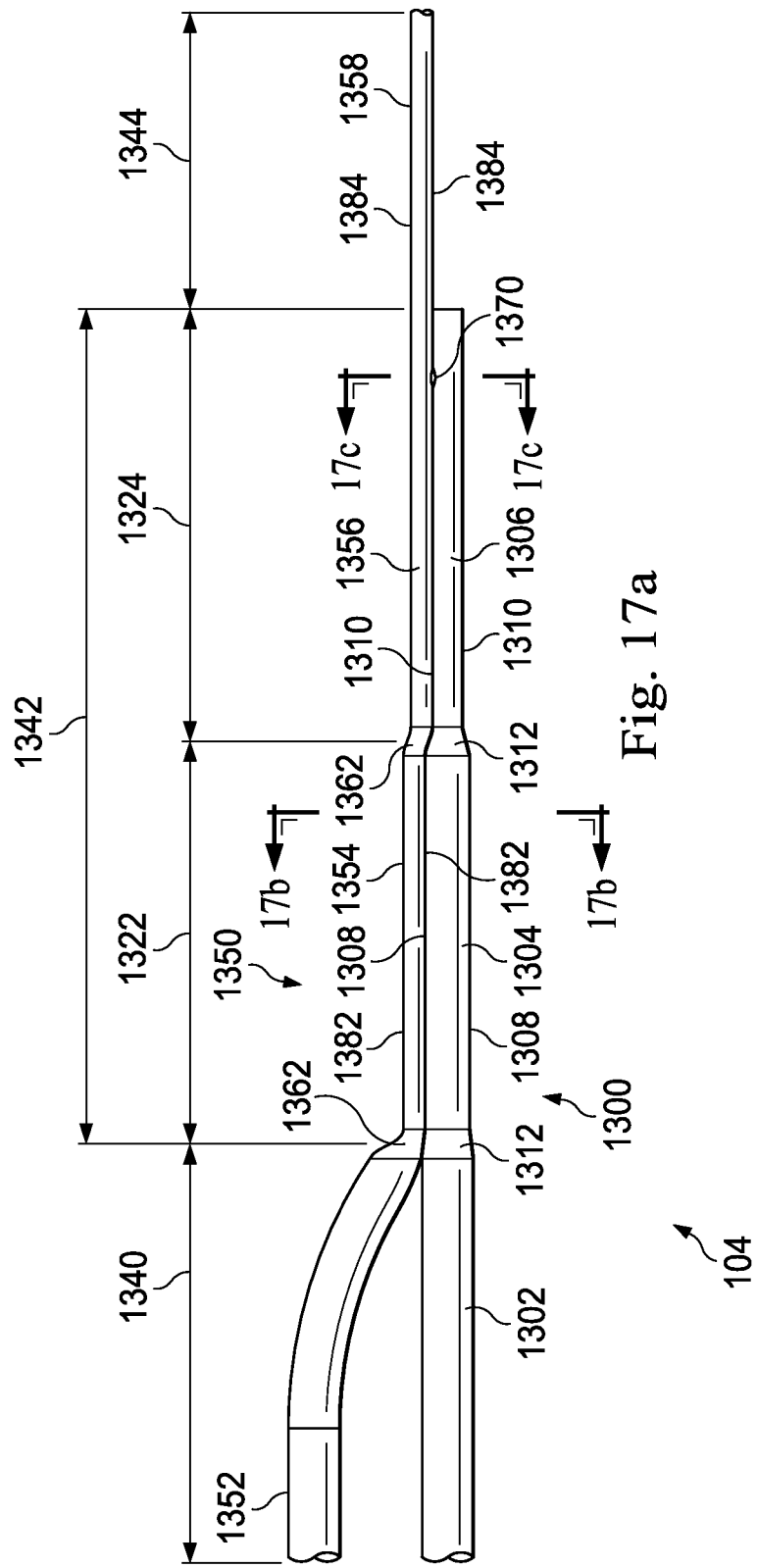
FIG. 17a is a diagrammatic side view of a distal portion of an intravascular device according to aspects of the present disclosure.
Figure 17B:
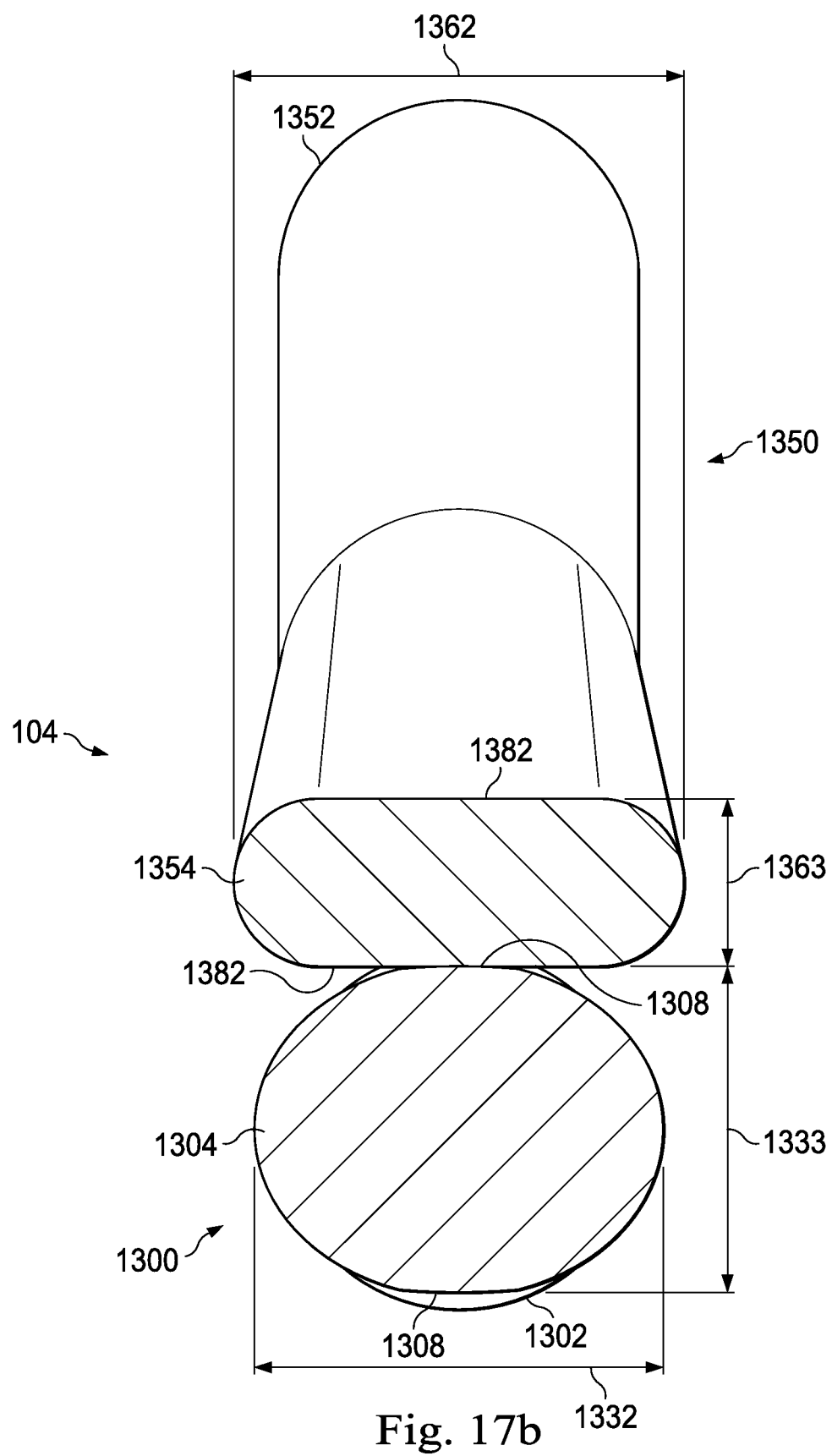
Figure 17C:
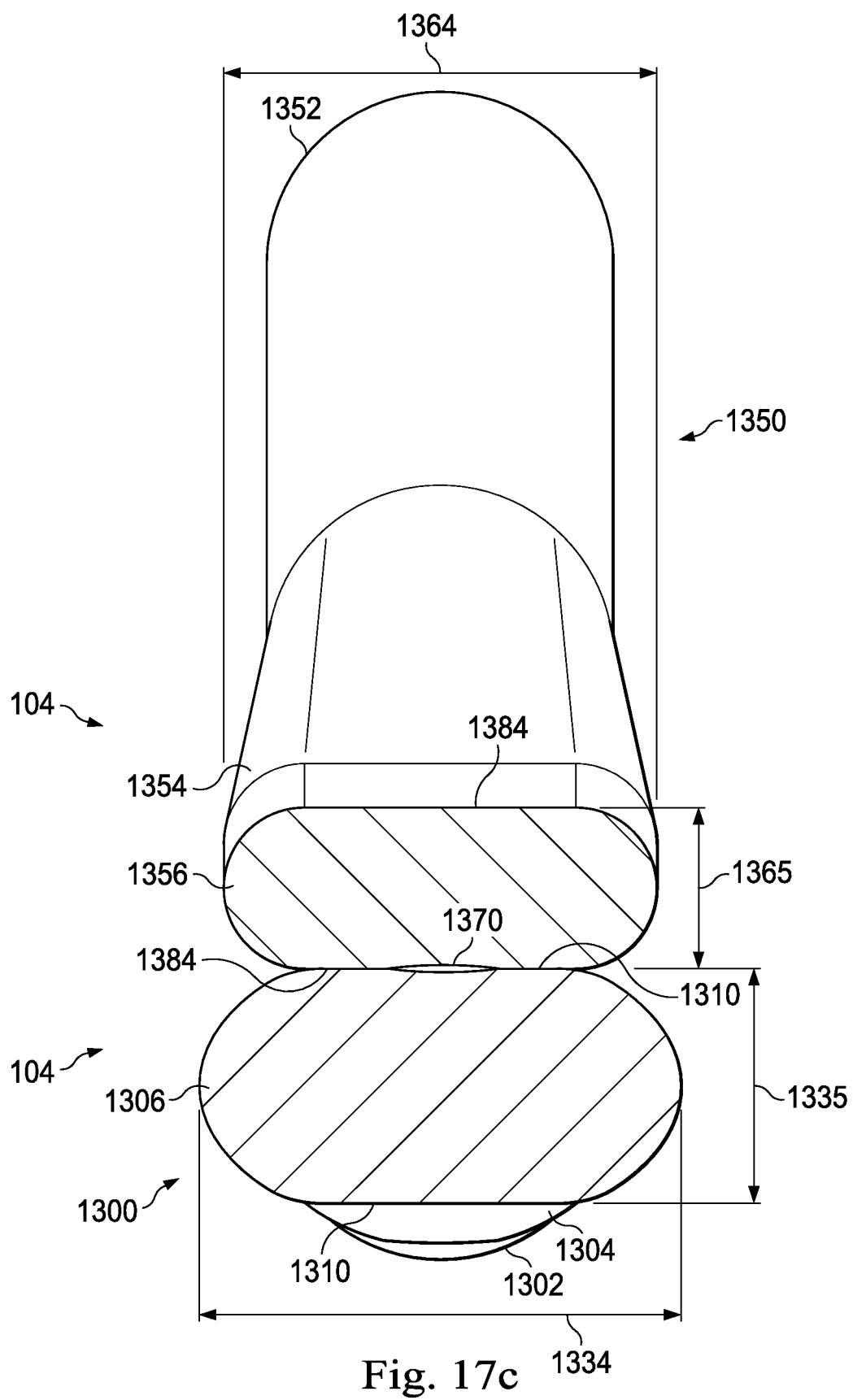

Referring again to FIG. 14, the method 1400 can include, at step 1440, shaping the first and second core wires to include respective at least two flattened sections. As illustrated in FIGS. 17*a*-17*c*, the core wire 1300 includes flattened sections 1304, 1306, and the core wire 1350 can include flattened sections 1354, 1356. Shaping the distal portion of the core wire 1300 can occur simultaneously shaping the core wire 1350. Shaping the distal portion of the core wires 1300, 1350 can include cold forming the respective at least two flattened sections, such as by pressing core wires 1300, 1350 with suitable dies. Because the core wire 1350 is coupled to the distal portion of the core wire 1300 (step 930), pressure can be simultaneously applied to both the core wires 1300, 1350 to the form the respective at least two flattened sections. The core wires 1300, 1350 can be shaped such that the respective flattened sections are longitudinally aligned. In other embodiments, shaping the core wires 1300, 1350 can include grinding, ablating, and/or cutting.

In some embodiments, the method 1400 can include introducing solder between the core wires 1300, 1350 as pressure is being simultaneously applied to the core wires 1300, 1350. For example, solder can be introduced at a distal most flattened section (e.g., flattened section 1306) of the core wire 1300. For example, solder can be introduced along two or more of the flattened sections (e.g., flattened sections 1304, 1306) of the core wire 1300. Introducing additional solder when the core wires 1300, 1350 are shaped can ensure that the coupling between the core wires remains after pressure is applied. For example, the bottom planar region 1384 of the flattened section 1356 of the core wire 1350 can be soldered to the top planar region 1310 of the core wire 1300 and/or the bottom planar region 1382 of the core wire 1350 can be soldered to the top planar region 1308 of the core wire 1300.

The flattened sections 1304, 1306 of the core wire 1300 can be similar to the respective flattened sections 304, 306 (FIG. 6*a*-6*d*) of the core wire 300 and/or the respective flattened sections 804, 806 (FIGS. 12*a*-12*c*) of the core wire 800. For example, the lengths 1322, 1324 of the respective flattened sections 1304, 1306 can be between about 0.1 cm and about 1 cm, about 0.1 cm and 0.8 cm, about 0.1 cm and 0.6 cm, etc., including values such as 0.5 cm, 0.6 cm, 0.8 cm, etc. In some embodiments, a combined length 1342 of the flattened sections 1304, 1306 is the same regardless of the whether the individual lengths 1322, 1324 are the same or different. For example, the combined length 1342 can be 1 cm. A reduced diameter section 1302 can be similar to the reduced diameter section 1302 (FIGS. 6*a*-6*b*). For example, a length 1340 of the reduced diameter section 1302, between the housing 109 and the proximal most transition region 1312 can be, for example, 1 cm.

While only two flattened sections 1304, 1306 of the core wire 1300 are illustrated, it is understood that the core wire 1300 can include one flattened section, or three or more flattened sections in different embodiments. The core wire 1300 can be shaped such that the flattened section 1304 includes planar regions 1308 and the flattened section 1306 includes planar regions 1310. The planar regions 1308, 1310 can be similar to the planar regions 308, 310 (FIGS. 6a-6d) and/or the planar regions 808, 810 (FIGS. 12a-12c).

The cross-sectional profiles of the flattened sections 1304, 1306 can be different from each other and different from the cross-sectional profile of the reduced diameter section 1302. The cross-sectional profiles of the flattened sections 1304, 1306 and the reduced diameter section 1302 can be similar to the respective cross-sectional profiles of the flattened section 304, 306 and the reduced diameter section 302, and/or the respective cross-sectional profiles of the flattened sections 804, 806, and the reduced diameter section 802. In that regard, the cross-sectional profile of the flattened portion 1304 can be taller than the cross-sectional profile of the flattened portion 1306. For example, the height 1333 of the flattened portion 1304 can be between about 0.001" and 0.003", about 0.001" and 0.002", etc., including values such as 0.0015", 0.00175", 0.002", etc. For example, the height 1335 of the flattened portion 1306 can be between about 0.001" and 0.003", about 0.001" and 0.002", etc., including values such as 0.00125", 0.0015", 0.00175", etc. The cross-sectional profile of the flattened portion 1304 can be wider than the cross-sectional profile of the flattened portion 1306. For example, the width 1332 of the flattened portion 1304 can be between about 0.001" and 0.005", about 0.001" and 0.003", etc., including values such as 0.0015", 0.002", 0.0025", etc. For example, the width 1334 of the flattened portion 1306 can be between about 0.001" and 0.005", about 0.001" and 0.003", etc., including values such as 0.002", 0.00225", 0.0025", etc.

The flattened sections 1354, 1356 of the core wire 1350 can include planar regions 1382, 1384, respectively. The planar regions 1382, 1384 can be similar to the planar regions 384 (FIG. 7b-7c) and/or planar regions 882, 884 (FIGS. 12a-12c). Generally, in the illustrated embodiment of FIGS. 17a-17c, the cross-sectional profiles of the flattened sections 1354, 1356 are substantially oval shaped. The cross-sectional profiles can also be described as rectangular with rounded sides. In some embodiments, the dimensions of the cross-sectional profiles and/or the cross-sectional areas of the flattened sections 1354, 1356 are the same or similar. In some embodiments, the dimensions of the cross-sectional profiles and/or the cross-sectional areas of the flattened sections 1354, 1356 are different. For example, the height of the flattened section 1354 can be greater than the height of the flattened section 1356. For example, the height 1363 of the flattened portion 1354 can be between about 0.001" and 0.003", about 0.001" and 0.002", etc., including values such as 0.0015", 0.00175", 0.002", etc. For example, the height 1365 of the flattened portion 1356 can be between about 0.001" and 0.003", about 0.001" and 0.002", etc., including values such as 0.00125", 0.0015", 0.00175", etc. For example, the width of the flattened section 1356 can be greater than the width of the flattened section 1354. For example, the width 1362 of the flattened portion 1354 can be between about 0.001" and 0.005", about 0.001" and 0.003", etc., including values such as 0.0015", 0.002", 0.0025", etc. For example, the width 1364 of the flattened portion 1356 can be between about 0.001" and 0.005", about 0.001" and 0.003", etc., including values such as 0.002", 0.00225", 0.0025", etc. While only two flattened sections 1354, 1356 of the core wire 1350 are illustrated, it is understood that the core wire 1350 can include one flattened section, or three or more flattened sections in different embodiments.

In the at least partially assembled configuration shown in FIGS. 17a-17c, the distal portion 1358 of the core wire 1350 can extend distally from the core wire 1300 and/or the solder joint 1370. The distal portion 1358 can terminate at and be coupled to the distal tip 111. A proximal portion 1352 can extend proximally from the solder joint 1370 and/or the proximal most flattened section (e.g., flattened section 1354) of the core wire 1350. The proximal portion 1352 can terminate at and be coupled to the housing 109 (FIG. 2) and/or adhesive within and/or surround the housing 109. The cross-sectional profiles of the proximal portion 1352 and the distal portion 1358 can be substantially circular (as was the entirety of the core wire 1350, as illustrated in FIGS. 16a-16b) because only cross-sectional profiles of the flattened portions 1354, 1356 was modified in step 1440. A length 1344 of the distal portion 1358 of the core wire 1350 (e.g., between the distal end of the core wire 1300 and the distal tip 111), the combined length 1342 of the flattened portions 1304, 1306 of the core wire 1300, and/or a length 1340 of the reduced diameter section 1302 of the core wire 1300 (e.g., between the housing 109 and the proximal most flattened section) can each be between about 0.1 cm and about 5 cm, about 0.1 cm and 2 cm, about 0.1 cm and 1 cm, etc., including values such as 0.5 cm, 1 cm, 1.5 cm, etc. The lengths 1340, 1342, 1344 can be similar to the lengths 340, 342, 344 (FIGS. 7a-7b) and/or the lengths 840, 842, 844 (FIGS. 12a-12c).

In some embodiments, the method 1400 can include additional steps to incorporate the element 108 within the intravascular device 100. For example, the method 1400 can include coupling the housing 109 to the core wire 1300, when the housing 109 is a separate component. The method 1400 can include forming a recess within the core member 1300. The recess can be sized and shaped to accommodate the element 108. The method 1400 can also include coupling the element 108 to the core member 1300 (e.g., within the housing 109 or within the recess formed within the core member 1300). The element 108 can be positioned at a distal portion of the core member 1300. The method 1400 can include various other steps to complete assembly of the intravascular device 100, including electrically coupling the element 108 to other component(s) of the intravascular device 100, introducing adhesive(s) into a lumen of the flexible elongate member 102, coupling the core member 120 and the core member 122, introducing a sleeve (e.g., with an integrated coil) around the flexible elongate member 102, introducing a tip coil around the distal portion 104, among others.

Guide wires of the present disclosure can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. For example, the features of various embodiments can be combined with features of different embodiments. One or more steps can be added to or removed from the methods described herein. A person of ordinary skill in the art will understand that the steps of the method can be performed in an order different than the order described herein. It is understood that such variations may be made to the foregoing without departing from the scope of the present disclosure. Accordingly, it is appropriate that the appended claims be construed broadly and in a manner consistent with the present disclosure.

What is claimed is:

1. A sensing guide wire, comprising:
a first flexible elongate member;
a sensor;
a housing structure attached to a distal portion of the first flexible elongate member, wherein the sensor is mounted to the housing structure; and
a second flexible elongate member comprising a proximal portion, a distal portion, and an intermediate portion between the proximal portion and the distal portion,
wherein the intermediate portion of the second flexible elongate member is attached to the first flexible elongate member at a first attachment location,
wherein the proximal portion of the second flexible elongate member terminates and is attached to the housing structure at a different, second attachment location spaced from and proximal to the first attachment location,
wherein the proximal portion of the second flexible elongate member is spaced from the first flexible elongate member at the second attachment location,
wherein the distal portion of the second flexible elongate member extends distally from the first flexible elongate member,
wherein the distal portion of the first flexible elongate member includes a flattened section,
wherein the first attachment location comprises a longitudinal surface of the flattened section, and
wherein the second flexible elongate member comprises a shaping ribbon.

2. The guide wire of claim 1, wherein the first flexible elongate member comprises a first core wire.

3. The guide wire of claim 1, wherein the sensor is at least one of a pressure sensor or a flow sensor.

4. The guide wire of claim 1, wherein a top surface of the first flexible elongate member is attached to a bottom surface of the second flexible elongate member.

5. The guide wire of claim 1, wherein a cross-sectional profile of the first flexible elongate member is rectangular with rounded sides at the flattened section.

6. The guide wire of claim 1, wherein the longitudinal surface is planar.

7. The guide wire of claim 1, wherein the distal portion of the first flexible elongate member includes at least two flattened sections, wherein the at least two flattened sections comprise a proximal flattened section and a distal flattened section.

8. The guide wire of claim 7, wherein the first and second flexible elongate members are attached at the distal flattened section of the first flexible elongate member.

9. The guide wire of claim 7, wherein the first and second flexible elongate members are attached along more than one of the at least two flattened sections of the first flexible elongate member.

10. The guide wire of claim 7, wherein cross-sectional profiles of the at least two flattened sections are shaped differently.

11. The guide wire of claim 7, wherein a dimension of the distal flattened section of the first flexible elongate member is different from a dimension of the proximal flattened section.

12. The guide wire of claim 7,
wherein the proximal flattened section comprises a longitudinal surface and the distal flattened section comprises a longitudinal surface,
wherein the longitudinal surface of the flattened section is one of the longitudinal surface of the proximal flattened section or the longitudinal surface of the distal flattened section, and
wherein the longitudinal surface of the proximal flattened section and the longitudinal surface of the distal flattened section are adjacent to one another along a length of the first flexible elongate member.

13. The guide wire of claim 12, wherein a proximal portion of the first flexible elongate member includes a first cross-sectional area, wherein the proximal flattened section comprises a second cross-sectional area, wherein the distal flattened section comprises a third cross-sectional area, wherein the distal portion of the first flexible elongate member includes a transition region between the second cross-sectional area of the proximal flattened section and the third cross-sectional area of the distal flattened section.

14. The guide wire of claim 7, wherein the second flexible elongate member includes at least two flattened sections aligned longitudinally with the at least two flattened sections of the first flexible elongate member.

15. The guide wire of claim 14, wherein a cross-sectional profile of the second flexible elongate member is rectangular with rounded sides at the at least two flattened sections of the second flexible elongate member.

16. The guide wire of claim 14, wherein the at least two flattened sections of the second flexible elongate member comprise planar surfaces.

17. The guide wire of claim 1, wherein the first flexible elongate member is attached to the second flexible elongate member without an additional attachment member disposed about the first or the second flexible elongate member.

18. The guide wire of claim 1, wherein the housing structure comprises a tubular structure.

19. The guide wire of claim 18, wherein the housing structure comprises a portion of the first flexible elongate member extending through the tubular structure.

20. A sensing guide wire, comprising:
a first flexible elongate member;
a sensor;
a housing structure attached to a distal portion of the first flexible elongate member, wherein the sensor is mounted to the housing structure; and
a second flexible elongate member comprising a proximal portion, a distal portion, and an intermediate portion between the proximal portion and the distal portion,
wherein the intermediate portion of the second flexible elongate member is attached to the first flexible elongate member at a first attachment location,
wherein the proximal portion of the second flexible elongate member terminates and is attached to the housing structure at a different, second attachment location spaced from and proximal to the first attachment location,
wherein the proximal portion of the second flexible elongate member is spaced from the first flexible elongate member at the second attachment location, and wherein the distal portion of the second flexible elongate member extends distally from the first flexible elongate member, wherein the first attachment location comprises a longitudinal surface of the flattened section, wherein the distal portion of the first flexible elongate member includes at least two flattened sections, wherein the at least two flattened sections comprise a proximal flattened section and a distal flattened section, wherein the second flexible elongate member includes at least two flattened sections aligned longitudinally with the at least two flattened sections of the first flexible elongate member.

21. The guide wire of claim 20, wherein the second flexible elongate member comprises a second core wire.

22. The guide wire of claim 20, wherein a cross-sectional profile of the second flexible elongate member is rectangular with rounded sides at the at least two flattened sections of the second flexible elongate member.

23. The guide wire of claim 20, wherein the at least two flattened sections of the second flexible elongate member comprise planar surfaces.

24. The guide wire of claim 20, wherein the first flexible elongate member comprises a first core wire.

25. The guide wire of claim 20, wherein the second flexible elongate member comprises a shaping ribbon.

26. The guide wire of claim 20, wherein the first and second flexible elongate members are attached at the distal flattened section of the first flexible elongate member.

27. The guide wire of claim 20, wherein the first and second flexible elongate members are attached along more than one of the at least two flattened sections of the first flexible elongate member.

28. The guide wire of claim 20, wherein cross-sectional profiles of the at least two flattened sections of the first flexible elongate member are shaped differently.

29. The guide wire of claim 20, wherein a dimension of the distal flattened section of the first flexible elongate member is different from a dimension of the proximal flattened section.

30. The guide wire of claim 20, wherein the sensor is at least one of a pressure sensor or a flow sensor.

31. The guide wire of claim 20, wherein a top surface of the first flexible elongate member is attached to a bottom surface of the second flexible elongate member.

32. The guide wire of claim 20, wherein a cross-sectional profile of the first flexible elongate member is rectangular with rounded sides at the at least two flattened sections of the first flexible elongate member.

33. The guide wire of claim 20, wherein the longitudinal surface is planar.

34. The guide wire of claim 20,
wherein the proximal flattened section comprises a longitudinal surface and the distal flattened section comprises a longitudinal surface,
wherein the longitudinal surface of the flattened section is one of the longitudinal surface of the proximal flattened section or the longitudinal surface of the distal flattened section, and
wherein the longitudinal surface of the proximal flattened section and the longitudinal surface of the distal flattened section are adjacent to one another along a length of the first flexible elongate member.

35. The guide wire of claim 34, wherein a proximal portion of the first flexible elongate member includes a first cross-sectional area, wherein the proximal flattened section comprises a second cross-sectional area, wherein the distal flattened section comprises a third cross-sectional area, wherein the distal portion of the first flexible elongate member includes a transition region between the second cross-sectional area of the proximal flattened section and the third cross-sectional area of the distal flattened section.

36. The guide wire of claim 20, wherein the first flexible elongate member is attached to the second flexible elongate member without an additional attachment member disposed about the first or the second flexible elongate member.

37. The guide wire of claim 20, wherein the housing structure comprises a tubular structure.

38. The guide wire of claim 37, wherein the housing structure comprises a portion of the first flexible elongate member extending through the tubular structure.

* * * * *